(12) United States Patent
Walley

(10) Patent No.: US 8,134,133 B1
(45) Date of Patent: Mar. 13, 2012

(54) METHOD AND SYSTEM FOR AUTHENTICATING ARCHEOLOGICAL ARTIFACTS

(76) Inventor: David Hunter Walley, Fulton, MS (US)

( * ) Notice: Subject to any disclaimer, the term of this patent is extended or adjusted under 35 U.S.C. 154(b) by 0 days.

(21) Appl. No.: 12/472,333

(22) Filed: May 26, 2009

Related U.S. Application Data

(60) Provisional application No. 61/056,050, filed on May 26, 2008.

(51) Int. Cl.
*G01J 1/58* (2006.01)
(52) U.S. Cl. .................................. 250/459.1; 250/458.1
(58) Field of Classification Search ............... 250/458.1, 250/459.1; 356/326
See application file for complete search history.

(56) References Cited

U.S. PATENT DOCUMENTS

| | | | | |
|---|---|---|---|---|
| 6,178,227 | B1 * | 1/2001 | Sato | 378/117 |
| 6,295,333 | B1 * | 9/2001 | Tamura | 378/44 |
| 7,001,038 | B2 * | 2/2006 | Bock et al. | 362/125 |
| 7,042,567 | B2 * | 5/2006 | Balas et al. | 356/326 |
| 7,364,317 | B2 * | 4/2008 | Bock et al. | 362/125 |
| 2003/0117620 | A1 * | 6/2003 | Balas et al. | 356/326 |
| 2004/0141320 | A1 * | 7/2004 | Bock et al. | 362/253 |
| 2006/0098435 | A1 * | 5/2006 | Bock et al. | 362/253 |
| 2007/0274455 | A1 * | 11/2007 | Tarawneh et al. | 378/177 |
| 2008/0037018 | A1 * | 2/2008 | Hoffmann | 356/405 |
| 2008/0170385 | A1 * | 7/2008 | Bock et al. | 362/125 |

* cited by examiner

*Primary Examiner* — Mark R Gaworecki
(74) *Attorney, Agent, or Firm* — Michael D. Eisenberg

(57) ABSTRACT

A method for authenticating an estimated age of an archaeological artifact is described. The method generally includes irradiating the artifact with laser light, measuring a fluorescence spectrum emitted from the artifact and determining whether the artifact's actual age is consistent with the estimated age based on the measured fluorescence.

20 Claims, 34 Drawing Sheets

---

IRRADIATE AN ARTIFACT WITH LASER LIGHT 200

IRRADIATE AN ETCHING ON THE ARTIFACT WITH LASER LIGHT 202

↓

MEASURE A FLUORESCENCE SPECTRUM EMITTED FROM THE ARTIFACT 205

↓

DETERMINE WHETHER THE ARTIFACT'S ACTUAL AGE IS CONSISTENT WITH THE ESTIMATED AGE BASED ON THE MEASURED FLUORESCENCE 210

METHOD AND SYSTEM FOR AUTHENTICATING ARCHEOLOGICAL ARTIFACTS

CROSS-REFERENCES TO RELATED APPLICATIONS

This application claims priority from U.S. Provisional Application Ser. No. 61/056,050 filed May 26, 2008, which is hereby incorporated herein by reference in its entirety.

TECHNICAL FIELD

The present invention relates to a method for authenticating an age of artifact or debunking the purported age of a fake artifact.

BACKGROUND OF THE INVENTION

Archaeological forgery is the manufacture of supposedly ancient items that are sold to the antiquities market and may even end up in the collections of museums. A string of archeological forgeries have usually followed news of prominent archaeological excavations. Historically, famous excavations like those in Crete, Valley of the Kings in Egypt and Pompeii have caused the appearance of a number of forgeries supposedly spirited away from the dig. Those have been usually presented in the open market but some have also ended up in museum collections and as objects of serious historical study. In recent times, forgeries of pre-Columbian pottery from the South America have been very common. Other popular examples include Ancient Egyptian earthenware and supposed ancient Greek gold.

Most of the archaeological forgery is made for money. The monetary value of an item that is thought to be thousands of years old is higher than the similar one sold as a souvenir. However, archaeological or paleontological forgers may have other motives; they may try to manufacture proof for their point of view, favorite theory or to gain increased frame and prestige for themselves. It may be used to create proof for religious history. Many known techniques used to detect forgeries require destroying a sample of the artifact. It would be desirable, therefore, for a method to be able to test for a forgery, without destroying part of the artifact if it does indeed turn out to be authentic.

BRIEF SUMMARY OF EMBODIMENTS OF THE INVENTION

According to one embodiment of the invention, a method for authenticating an estimated age of an archaeological artifact comprises: irradiating the artifact with laser light; measuring a fluorescence spectrum emitted from the artifact; and determining whether the artifact's actual age is consistent with the estimated age based on the measured fluorescence. In one embodiment, the method of authentication may further comprise irradiating an etching on the artifact with laser light. The term artifact may refer to an entire artifact as a whole or a particular feature of interest on an artifact such as an engraving, etching or writing.

In a variant, the method of authentication of may comprise: irradiating the artifact on a first area; measuring a fluorescence emitted from the first area; irradiating the artifact on a second area; measuring a fluorescence emitted from the second area; and comparing the fluorescence emitted from the first area with the emitted from the second area. The artifact's age is authenticated if an intensity of the fluorescence measured from the first area is greater than an intensity measured from the second area by a threshold amount. In one embodiment, the first area comprises a top surface layer of the artifact and the second area comprises a top surface layer of the artifact having been damaged by removal of part of the surface. The method may comprise removing a portion of the surface of the artifact.

In a further variant, the method of authentication may comprise: irradiating a surface of the artifact with laser light; measuring a fluorescence from the irradiated surface; focusing laser light at a depth below the surface and irradiating a point in the artifact at the depth; measuring a fluorescence from the irradiated point at depth; comparing the measured fluorescence from the irradiated surface with the measured fluorescence from the irradiated point at depth; and determining the authenticity of the artifact based on the comparison.

In still another variant, determining the authenticity of the artifact based on the comparison comprises determining whether an intensity of the fluorescence measured from the irradiated surface is greater than an intensity measured from the irradiated point at depth by a threshold amount.

In yet a further variant, the method may comprise using a virtual focus head laser to irradiate the point at depth and using a full contact head laser to irradiate a surface.

In another variant, the method may comprise irradiating a plurality of points on the surface of the artifact and measuring the fluorescence from the plurality of points on the surface. In one embodiment, the method may comprise using an automated mechanical device to position a laser over the plurality of points to irradiate, for example, a robot.

In a further variant, the method may include correlating the amount of fluorescence measured with the age of the artifact, wherein the artifact is of human origin. In one embodiment, correlating the amount of fluorescence measured with the age of the artifact comprises generating a spectrum of the measured fluorescence and comparing to a library of spectra and determining the authenticity of the artifact based on the comparison.

In still another variant, a system for debunking a purported age of an artifact comprises: a laser; a spectrometer configured for measuring fluorescence stimulated by laser light absorption of the artifact; and a computer configured to analyze the fluorescence measured by the spectrometer and determine whether the fluorescence measured meets a threshold amount. The computer is configured to display whether the fluorescence measured meets a threshold amount and wherein the purported age of the artifact is debunked if the measured fluorescence does not meet the threshold amount. In one embodiment, the laser emits light having 785 nanometer wavelengths.

In yet a further variant, the threshold amount is determined from a library of spectra from laser stimulated material of known approximate age ranges and compositions. In one embodiment, the system comprises a laser having virtual focus head and a laser having full contact head.

In another variant, a method for debunking a purported age of an artifact comprises determining the level of radiation damage in the surface of the artifact and comparing the level of radiation damage in the surface with the level of radiation damage in a reference material. The purported age of the artifact is debunked if the level of radiation damage in the surface of the artifact falls within a range determined by the reference material.

In a further variant of the method for debunking the age of an artifact, the reference material comprises the artifact itself, and the method further comprises comparing the level of radiation damage in the surface of the artifact with the level of radiation damage in an interior point of the artifact and below the surface of the artifact. The age of the of the artifact is debunked if the difference in radiation damage between the surface and the interior point is below a threshold amount. In one embodiment, the method determines the level of radiation damage in the surface of the artifact caused from the decay of a Radium 226 isotope. In a further variant the method comprises detecting a patina of radiation damage on the surface of the artifact.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

Figure 1:
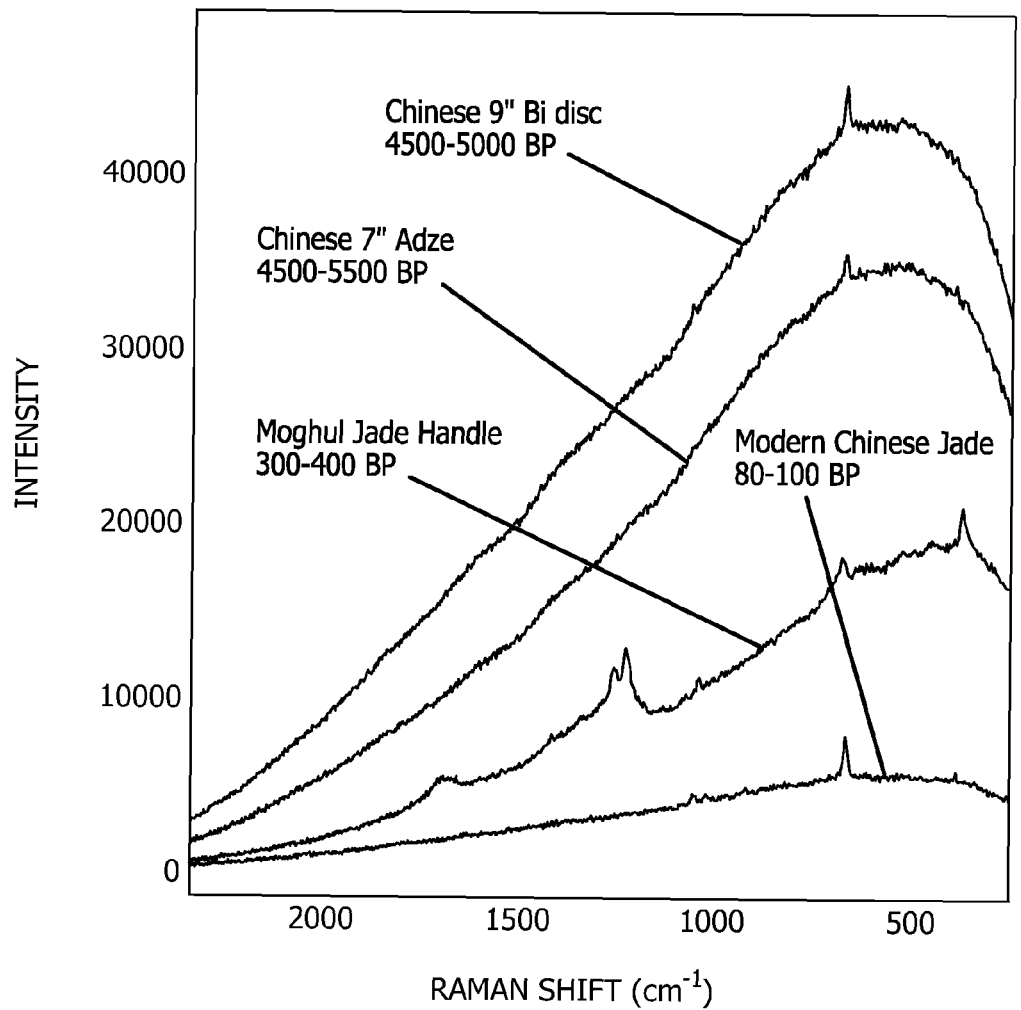
FIG. 1 is an illustration of the fluorescence measured from various aged artifacts.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

The present invention is directed toward a method for detecting age or antiquity in archaeological artifacts. The method may be used to authenticate the authenticity of etchings in old artifacts by demonstrating a disparity in age of the etching relative to the age of the overall artifact.

In one embodiment, the method may comprise a laser based Raman system in which the wavelength and power density are sufficient to liberate electrons captured in point, line, and void dislocations in organic and mineral material artifacts subjected to long term exposure to background radiation. Radiation damage may be induced by the natural Radium isotope present in the environment, and even more specifically, damage may be induced by the short-lived daughter, namely Radon 222 gas and its radioactive products, in the free state or solute in an aqueous phase percolating near and wetting the subterranean artifacts.

Disintegration of Radon 222 produces a 5.3 million electron volt (MEV) alpha particle with an immediate daughter Polonium 218, which in turn disintegrates into Lead 214 and Astatine 218, which generates a population of alpha and beta particles of various energy levels. This constant flux of radioactivity, combined in aqueous phase solution, produces a wetting and penetration into the artifact's surface as long as the average pore space of the material is larger than the molecular diameter of water combined with the atomic diameter of the solute, which is characteristic of Radon gas and its family of daughters. This allows Radon to diffuse a short distance and disintegrate within the artifact material and produce radiation damage in the artifact. This thin shell of radiation damage in the artifact is hereinafter referred to as "patina".

The method of the present invention further comprises subjecting the patinated artifact to a flux of laser light stimulation, such that the combined wavelength and power density are sufficient to liberate electrons in point, line, and void dislocations. The liberating and subsequent recombination of an orbital electron produces bursts of light photons. These bursts of light may be analyzed by a Raman spectrometer. The Raman spectrometer records the light bursts in real time on a spectrum analyzer and are displayed as fluorescence on a Raman output graph. The intensity of the fluorescence can be correlated to the age or antiquity of the artifact.

The present method further comprises consideration of micro-chemical erosion of the surrounding soil containing nano-structures with electron traps in situ eroding from radiation damaged minerals and the re-deposition of the nano-electron traps into and on the surface of the artifact. The means by which chemical dissolution and precipitation occur depends on the ph of the soil in question. This precipitation can occur and invade a mineralized structure from the bacteriological decomposition of protein gel left over as a result of larvae residue resulting from post-mortem effects whether human or animal. Three mechanisms are described for formation of a patina or skin effect. The patina ultimately produces fluorescence which includes the overall combination of radiation effects, which include decomposition of spatially distributed radiation damaged nano-structures and the precipitation within and on the surface of the artifact as well as the low incidence high radiation effect and the high incidence low radiation skin effect. This threefold effect contributes to the total fluorescence seen on a Raman spectrograph which detects antiquity in the archaeological artifact.

The method may further comprise detection of antiquity in metal artifacts, such as, for example, the noble metals on a periodic table of the chemical elements which include gold, silver, and copper. When buried, these metals acquire a shell of patina as described above. Gold is the most resistant to corrosion while copper is the least resistant and the corrosion of the metals governed by the Nernst equation for REDOX reactions and this is well known in the art. When these metals are buried and acquire radiation damage, a response on a Raman spectrograph would show a large intensity fluorescence spectrum and can be used to detect age or antiquity in the metal. Data regarding the fluorescence spectra can be obtained from thousands of known objects having various dates of creation and varying composition and can be stored in a library for comparison in determining authenticity of an unknown artifact.

Skin or shell of patina may be produced by low energy nuclear disintegration and heavy radiation effects caused by natural decomposition of fissionable materials or radiation produced by nuclear reactors. Fluxing of targets with radiation on the order of 200MEV from a fission reaction produces deep penetrating damage in targets much deeper and an order of magnitude deeper in the range of centimeters and tens of centimeters into a target. However, the probability and reduced incidence of these reactions in nature contribute less to the overall skin effect of patina described herein. Therefore, the current teaching of the present invention takes into account the twofold effect of radiation fluxing the target, which includes the slight fluorescence or skin effect from low incidence high energy radiation fluxing in combination with the high fluxing of weak radiation produced from the decomposition of the Radon 222 isotope and all the radiation supplied by the family of daughters from this isotope which ultimately produces the overall fluorescence in the patina as shown on the Raman spectrograph.

A further method of the present invention is to use the laser based Raman system at different wavelengths, such as for example 532, 785, and 1064 nanometers (nm). The wavelength is chosen depending on the response by a particular artifact to study. For example, since 785 nm is slightly infrared (IR), problems can arise in targeting black materials and minerals, because they possess black body absorption in the IR range of wavelength and quench the intensity of the Raman fluorescence reaction seen on the Raman spectrograph. Therefore, when the Raman fluorescence is low in a black body surface using 785 nm and 1064 nm, it is advantageous to switch to a 532 nm visible green laser. However, the Raman fluorescence generated using IR lasers to stimulate blackbody artifacts is in the range of an order of magnitude less than for non-blackbody absorbers. An example is a carbon and quartz sample. On the other hand, light colored crystalline materials comprising calcium carbonate, such as marble and alabaster have a good response with IR stimulation and produce large intensities of Raman fluorescence depending on the antiquity of the artifact.

Furthermore, when stimulating blackbody absorbers with an IR Laser Raman system, the power output can be increased to overcome the quenching of the Raman fluorescence, and for example, this power output may be in the range of 1 milliwatt (mw) to 500 mw and more preferably in the range 50-250 mw.

The method of the present invention may serve as a nondestructive test on the artifact wherein the power density of the incident laser light may be in the range of 25 watts per square centimeter and up to 6250 watts per square centimeter and more preferably in the range of 150 and 3000 watts per square centimeter. Above this range the surface of the material can be overheated and can cause micro-spalls or ablation of the surface. Artifact examples withstanding this effect effectively comprise refractory types of materials such as for example, ceramics, sandstones, granites, pipestones, obsidian and steatite or any igneous minerals born from high temperature geologic conditions. Therefore, the present invention includes the use of wavelength monochromatic laser having a particular power density to produce the Raman fluorescence intensity curve on the Raman output graph, wherein the intensity of Raman fluorescence relates to the latent radiation damage in the artifact and ultimately relates to the antiquity of the artifact or the antiquity of etching on the artifact.

The method of the present invention may further comprise multiple datapoint collection on an artifact's surface. This can be achieved by single point scans in a random spatially distributed surface performed manually or data collection provided by robotic end effector scans across the surface of the artifact in the X-Y-Z coordinate space or R, theta, Z in 3¬D polar coordinate space. Scans in the robotic dynamic mode have a Raman laser head attached where the virtual focus point is projected in space in front of the head (i.e. a few millimeters in front of the head). The exact ranging and maintenance of the focus point on the artifact's undulating 3-D surface can be accomplished by using miniature radar proximity or ultrasonic sensors in a spaced array and particular frequencies that do not interfere with the data collection of the Raman system at laser frequencies of interest.

The robotic system can be used for generating finely detailed 3-D Raman signal and fluorescence maps on the artifacts surface and subsequent interpretation of the map will aid in detection of large differences in the skin patina or possible areas disturbed by modern restoration and manipulation of the surface, i.e. recarved areas as a possible forgers technique to increase the value of the artifact. Tests were performed in the dynamic mode manually on smooth surface materials and found that linear speeds in the range of 1 mm per second to 5 mm per second are easily achieved with materials having good signal or fluorescence response and low laser power, i.e. 25 mw. However, for higher scan speeds, higher laser powers may be used up to the range between 250 mw and 500 mw and this power and speed is sufficient to generate data without harming the artifact by the thermal effects described above.

Another method of the invention includes the detection of art forgeries comprising forged stone sculptures. The materials of the sculptures may include, but are not limited to: limestone, granite, basalt, onyx-marble, Mexican Tecali, travertine, serpentine, nephrite jade, jadeite, polycrystalline limestone marbles and polycrystalline amorphous alabasters, Cycladic marble, and stone materials utilized by the ancients from ancient quarries and ancient source quarries utilized by modern forgers. The method of the present invention may detect the difference between a modern stone sculpted forgery and an ancient work even if both works came from an ancient quarry. Furthermore, the method of the present invention may detect a modern recarved or reworked ancient sculpture because the fluorescence patterns induced by laser fluxing will have much lower intensities in the reworked areas and up to ten and twenty times lower intensities if the rework has effectively penetrated the shell of patina.

A reworked or recarved area of an ancient stone can further include addition of glyphic text or iconography to increase the value of a piece and can be referred to as a type of "Pastiche". In still a further embodiment of the present invention, the method may detect reworked organic materials such as conch and *spondylus* shell and the like and reworked metal artifacts, such as for example, gold, silver and copper. Moreover, the method of the present invention may detect a disturbance in the natural patinated skin on stone, shell and metal artifacts by analysis of the intensity of the fluorescence on the Raman spectrograph as well as detection of lack of antiquity in sculpted stone forgeries where the stone material was derived from an ancient quarry.

The following experiments were conducted using the method of the present invention. In the following description, the conventional radiocarbon age, BP, is calculated using the radiocarbon decay equation:

$$t = -8033 \ln(Asn/Aon)$$

Where $-8033$ represents the mean lifetime of 14C, Aon is the activity in counts per minute of the modern standard, Asn is the equivalent cpm for the sample, and ln represents the natural logarithm operator.

Experiment 1

The first experiment utilized a 785 nm Laser Raman M unit manufactured by Enwave Optronics positioned on samples with a full contact laser head. The focus point was optimized at the interface of the target. Four pieces of Nephrite Jade from Asia of various ages were procured for the experimental setup, and were, as follows: Ancient Chinese Bi, highly patinated 9" diameter (est. age: 4500-5000BP); Ancient Chinese Neolithic Adze highly patinated possibly HongShan culture (est. age: 4500-5500BP); A Moghul Nephrite Jade Knife handle (est. age: 30G-400BP); and a modern Chinese jade copy of a Zhou or Shang Dynasty amulet. The Laser was set at a maximum power of 50 mw output and was confirmed by a small commercial joule meter, integration set at 5, which is a background scan for about 5 seconds and Laser scan for 5 seconds. The meter was set in automatic mode, which allows automatic subtraction of background from the laser scan.

Referring to FIG. 1, a strong Raman signal was detected (Stokes and anti-Stokes scattering) at 369, 679, 1043 cm-1 for the Moghul jade handle. However, only the Raman signal at 679 cm-1 was seen in the Ancient Chinese Bi and Adze. This was due to the large fluorescence hump seen on the output graph, which overwhelms any Raman signal present. The maximum of the fluorescence occurs at around 600 cm-1. The increased fluorescence hump in each sample illustrates the increase of antiquity or age of the sample.

Experiment 2

Figure 2:
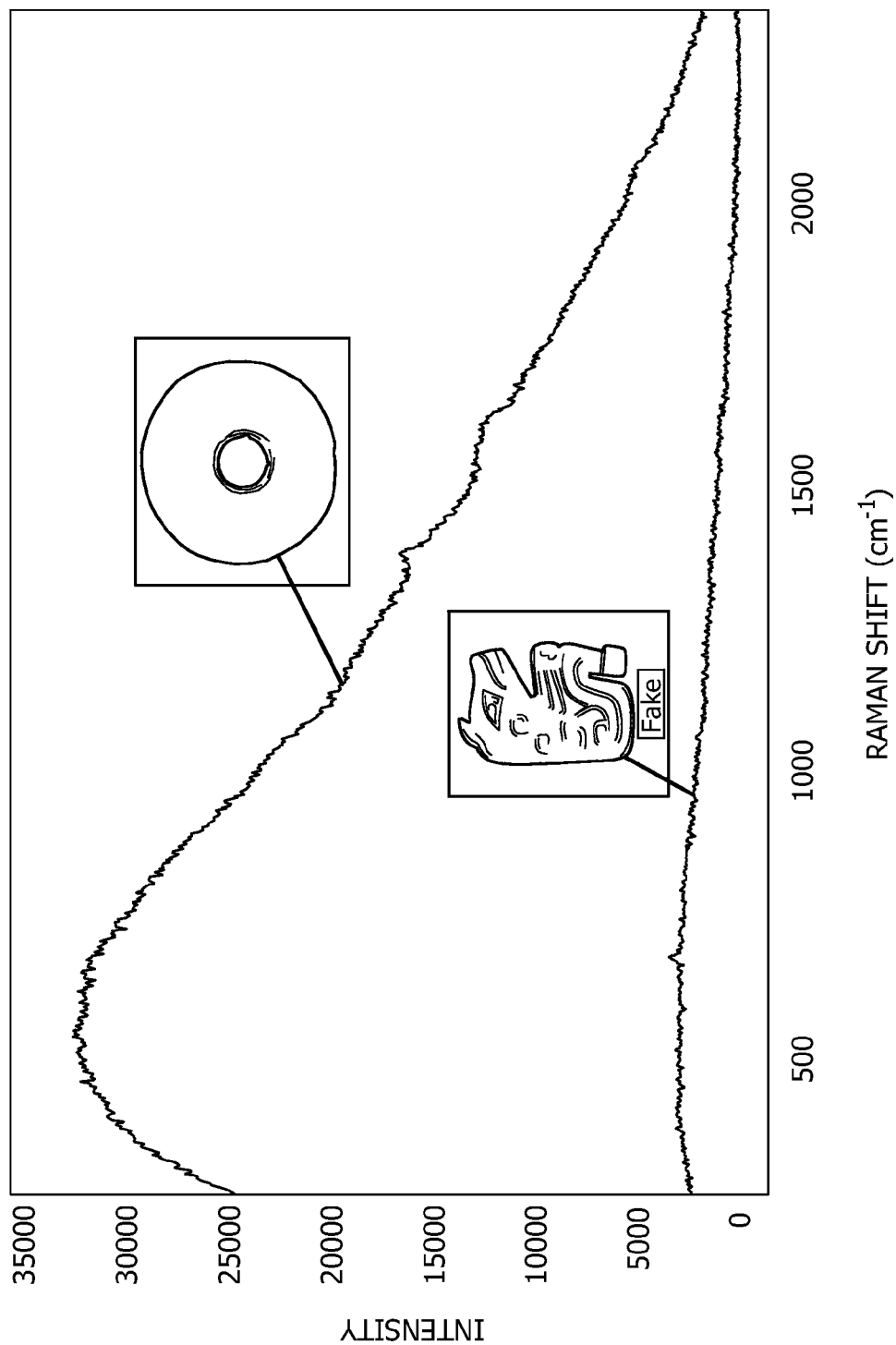
FIG. 2 is an illustration of the fluorescence measured from Ancient Chinese Bi against a fake Zhou or Shang Dynasty amulet.

Referring to FIG. 2, the object of experiment 2 was to retest the Ancient Chinese Bi against the fake or reproduction Zhou or Shang Dynasty amulet. Laser power was set at 25 mw and run for 5 integrations. The large difference in the fluorescence max can be seen around 500-600 cm--1 and illustrates the large difference in the antiquity of the targets.

Experiment 3

Figure 3:
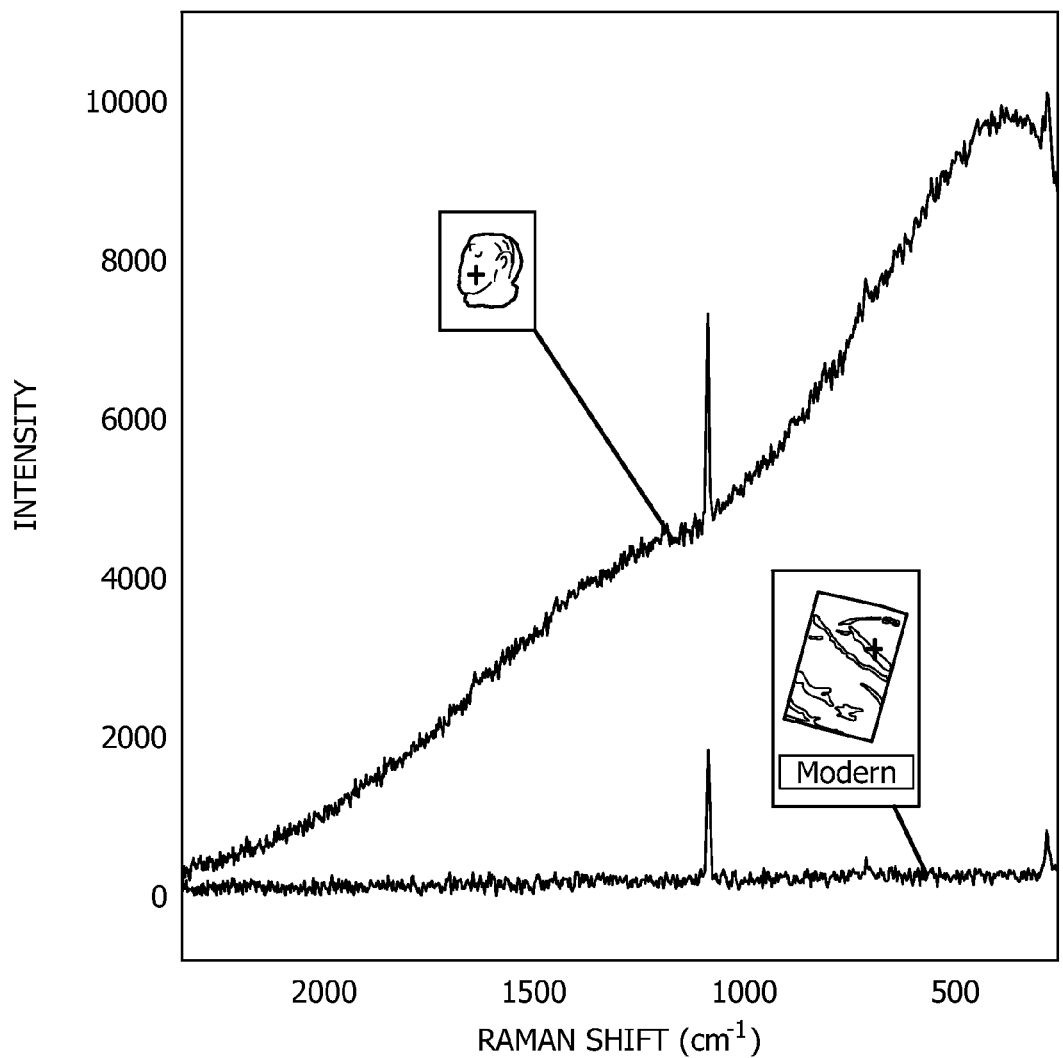
FIG. 3 is an illustration of the fluorescence measured from a small Greco-Roman marble with an estimated age of 2000-2200BP and a modern marble slab.

Referring to FIG. 3, the next experiment was set up to test polycrystalline calcium carbonate marble material. The laser was set at 50 mw power and 1 integration. A small Greco-Roman marble head of 1 and ½ inches (est. age: 2000-2200BP) was tested against a modern marble slab. The max in fluorescence of the Greco-Roman artifact was at 300-350 cm--1, illustrating the large difference in antiquity of the artifact with respect to the modern marble slab less than 10 years old.

Experiment 4

Figure 4:
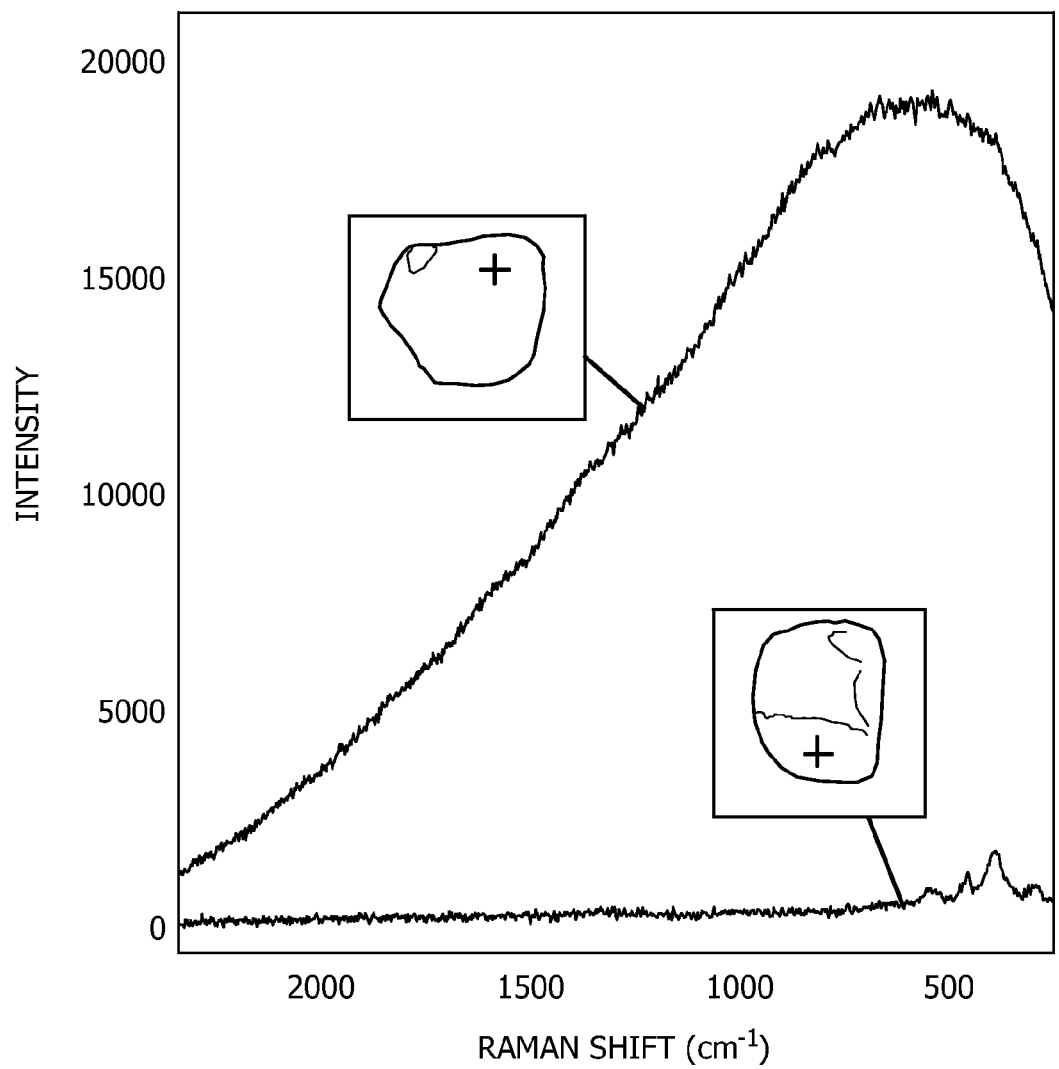
FIG. 4 is an illustration of the fluorescence measured from two areas (one with radiation damages and one with little damage) of a Native American nutting stone having estimated age of 2000-3000BP.

Referring to FIG. 4, experiment 4 was set up to test sandstone rock. The artifact was a small Native American nutting stone attributed to the Benton culture (est. age: 2000-3000BP). Laser scans were performed at 50 mw power, 1 integration on the old patinated surface with respect to a spall into the unpatinated core as a result of a plow's impact in the field. A strong Raman signal can be seen at 460 cm--1 on the unpatinated area which is attributable to the Laser light's interaction with a Silicone-Oxygen bond. However, on the highly patinated skin or shell of the artifact, the Raman effect at 460 cm--1 is completely masked over by fluorescence with a maximum at around 600 cm--1. This high fluorescence and lack of observed Raman effect is an indication of antiquity of the artifact.

Experiment 5

Figure 5:
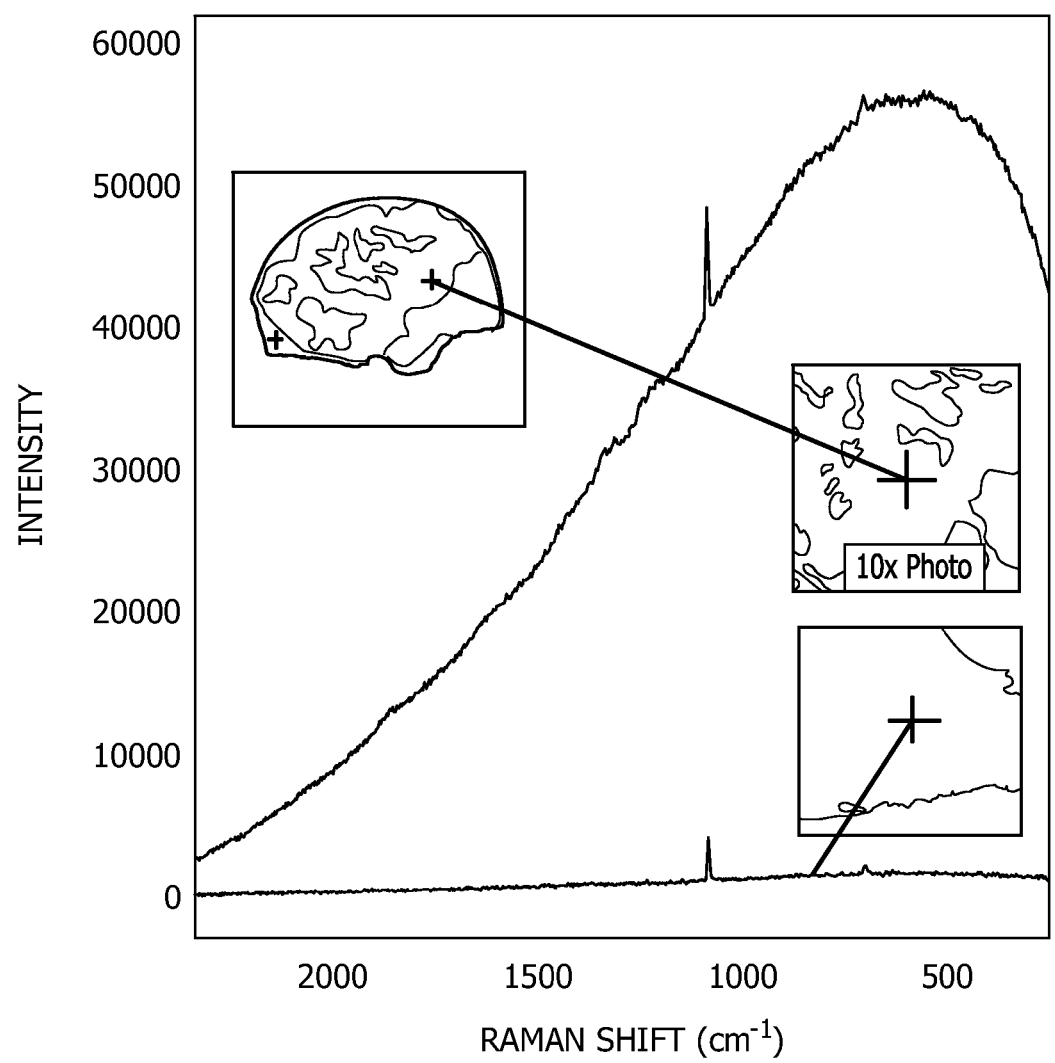
FIG. 5 is an illustration of the fluorescence measured from two areas (one with radiation damages and one with little damage) on an Archaeic Shell gorget fragment associated with flint projectile point types having an estimated age of 5000BP.

Referring to FIG. 5, experiment 5 was set up to test an Archaeic Shell gorget fragment associated with flint projectile point types (est. age: 5000BP). The laser was set at 50 mw and 1 integration time on two areas comprising the original patinated skin or shell of the outer surface and an area on the edge which had a 25 mil of an inch layer abraded off in order to scan the unpatinated core of the shell gorget. The high fluorescence of the of the outer surface with respect to the inner core illustrates the high degree of antiquity of the artifact. The results also serve as an example to of detecting a reworked or recarved ancient shell by a modern forger who may attempt application of iconographic glyphs or art in order to increase the value of the artifact. The present invention can detect the disturbance of the thin shell of patina on an ancient artifact.

Experiment 6

Figure 6:
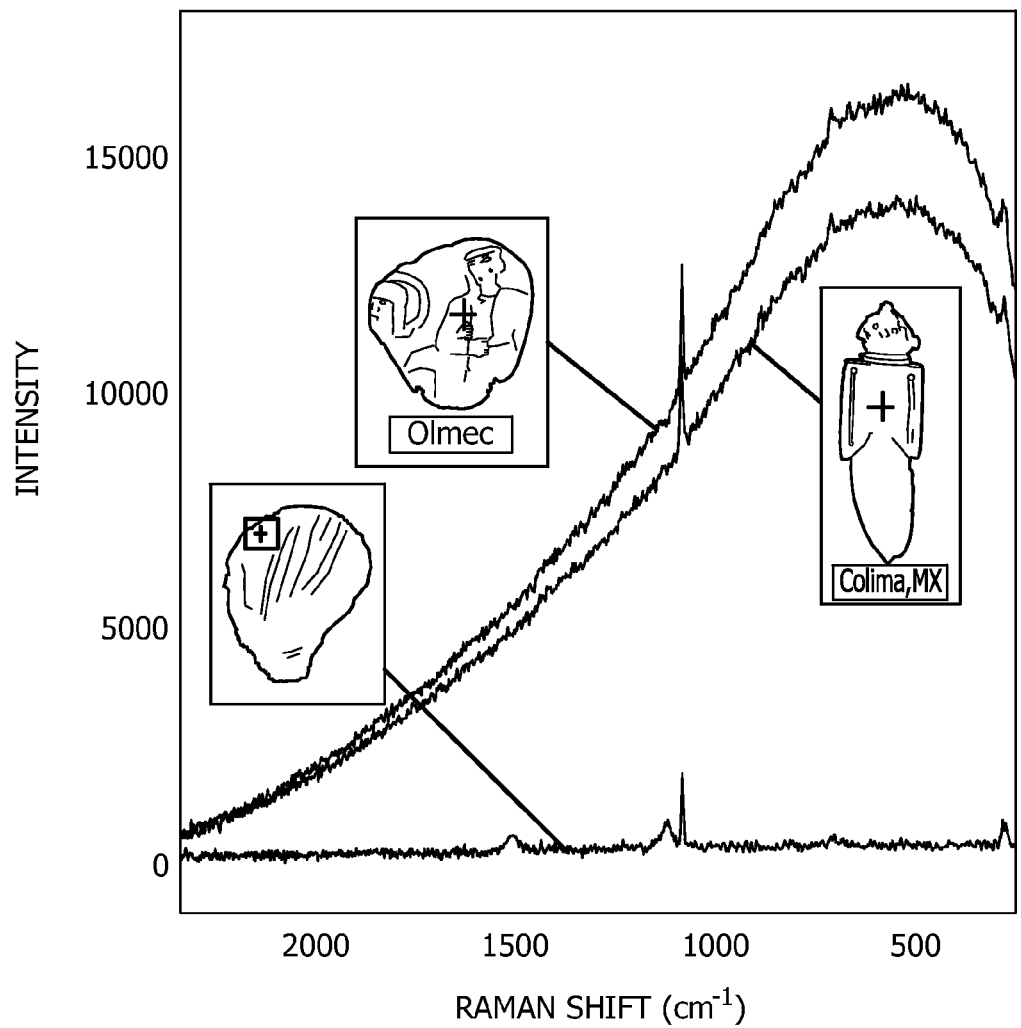
FIG. 6 is an illustration of the fluorescence measured from three pieces of *Spondylus* shell, two from the unabraded areas and one from an area having had a portion of the surface removed.

Referring to FIG. 6, experiment 6 was set up to further verify whether two ancient *Spondulus* shell carvings were reworked by a modern forger or whether the carvings and work were consistent with the period. Three pieces of *Spondylus* shell were tested, of which two were artifacts with carved iconographic details. The pieces were a pre-Columbian Olmec phase carving (est. age: 2500-2700BP), a pre-Columbian Colima phase vomiting spoon (est. age: 1800-2200BP), and a natural *Spondylus* trade shell at least 1500BP in age and had 50 mils removed from its natural *Spondylus* shell. A laser scan was run at 50 mw and 1 integration. No fluorescence was observed and good Raman effect was observed at 1100 cm--1, which corresponds to the interaction of the laser light with the bond in calcium carbonate present in the shell matrix. In comparison, the other two artifacts were tested and large fluorescence signals were seen indicating great age or a high degree of relative antiquity in the carved areas and are consistent with stylistic designs of the two pre-Columbian cultures.

Experiment 7

Figure 7:
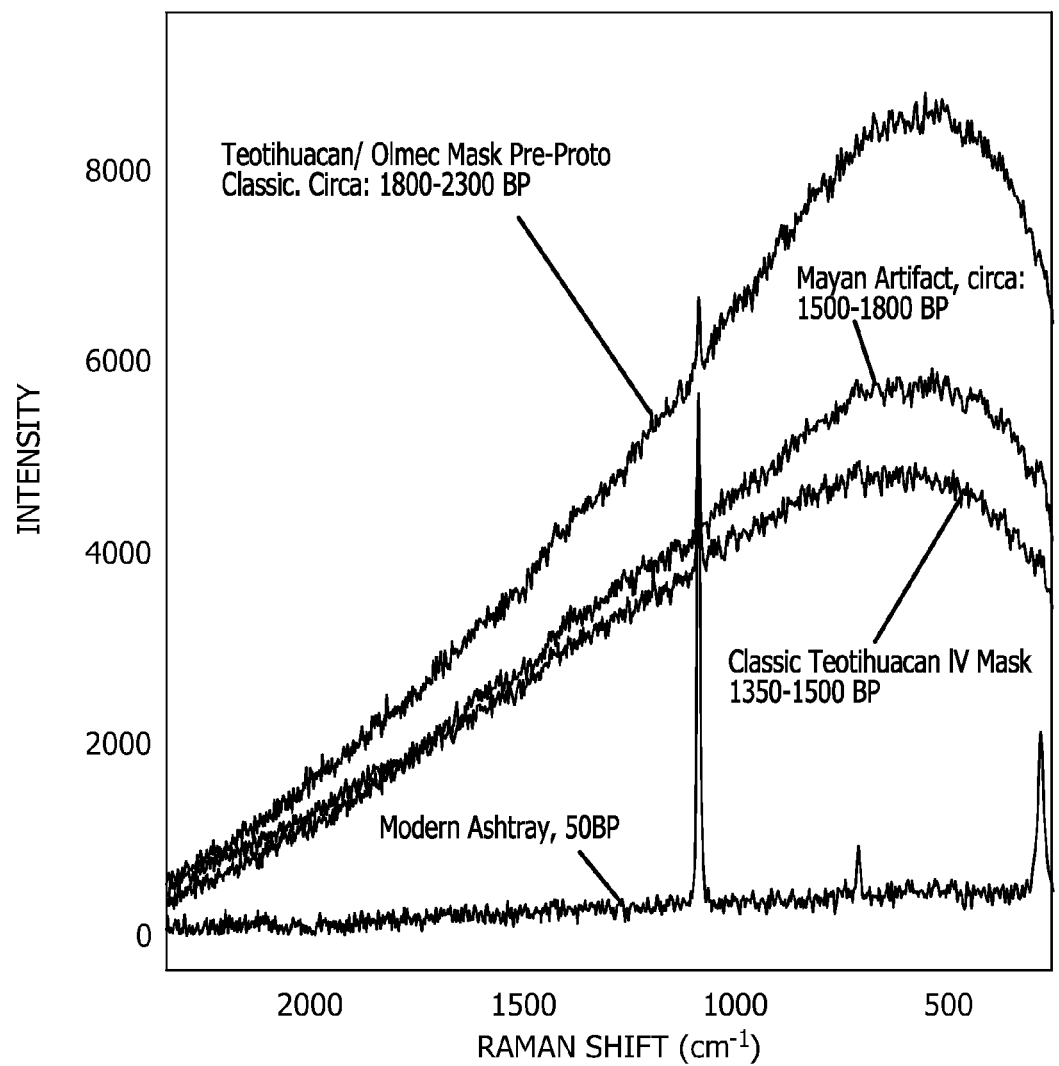
FIG. 7 is an illustration of the fluorescence measured from several antique artifacts and a modern object.
Figure 8A:
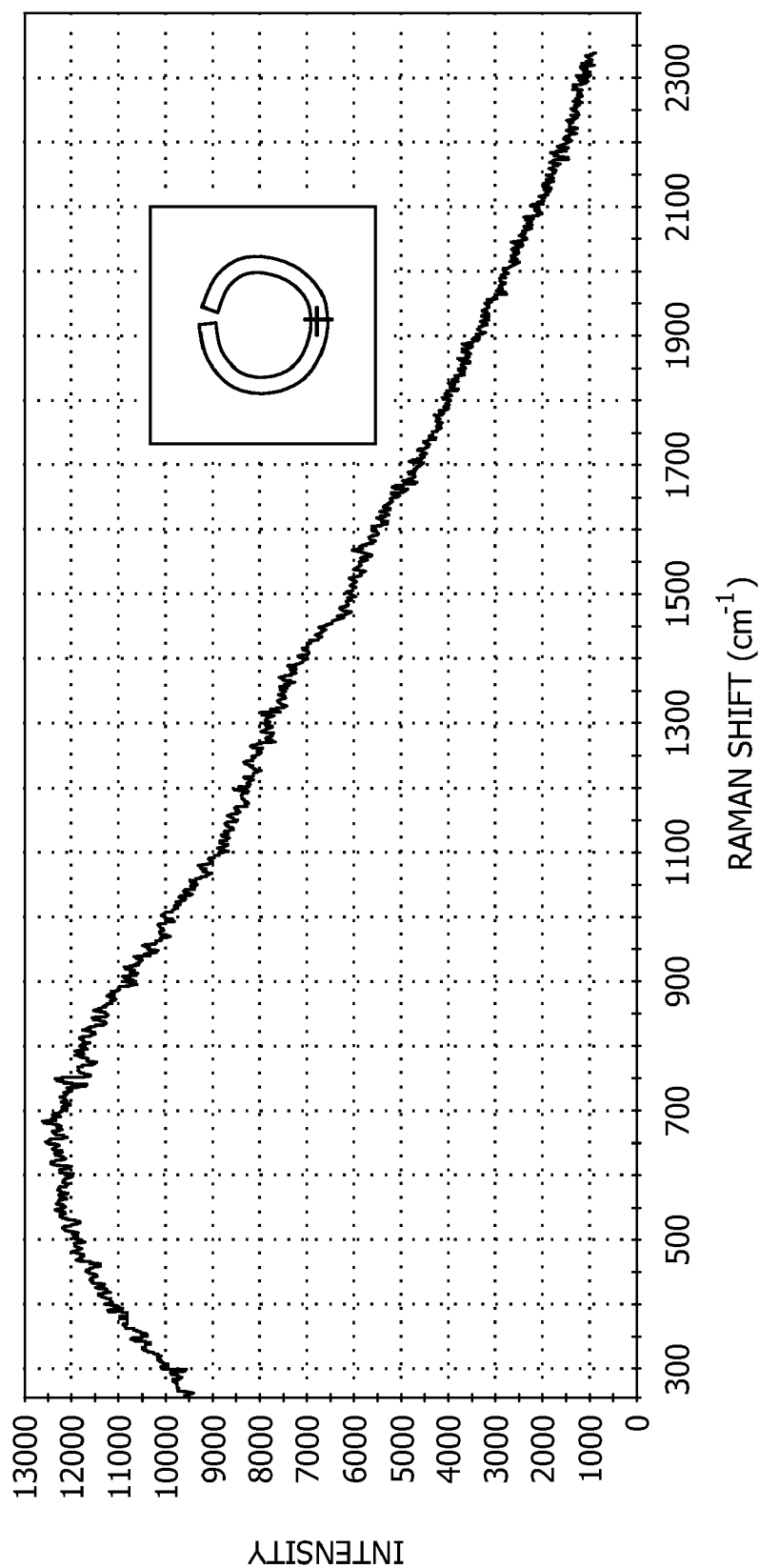
FIGS. 8A-8D are illustrations of the fluorescence measured from several antique gold pieces and a modern gold piece.
Figure 8B:
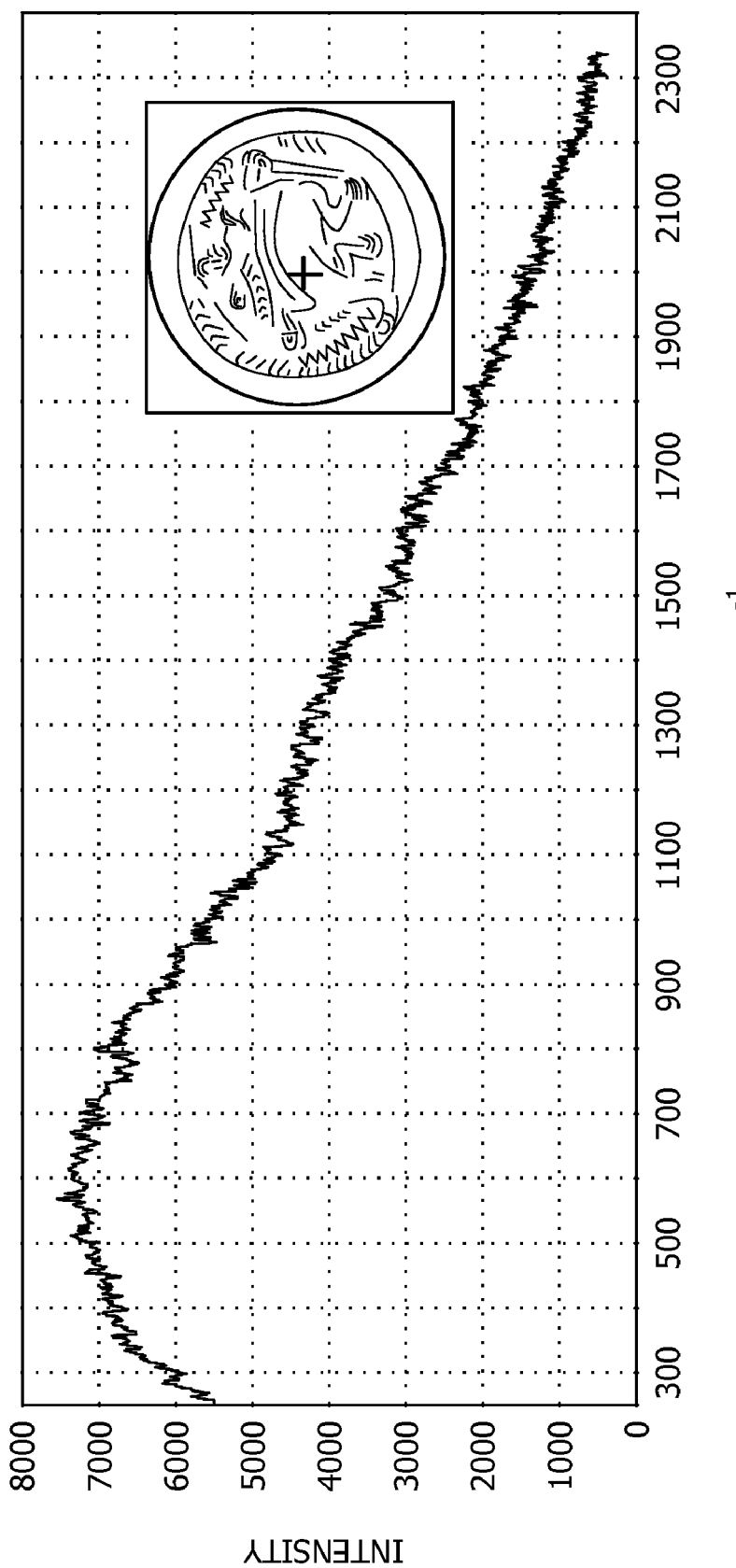
Figure 8C:
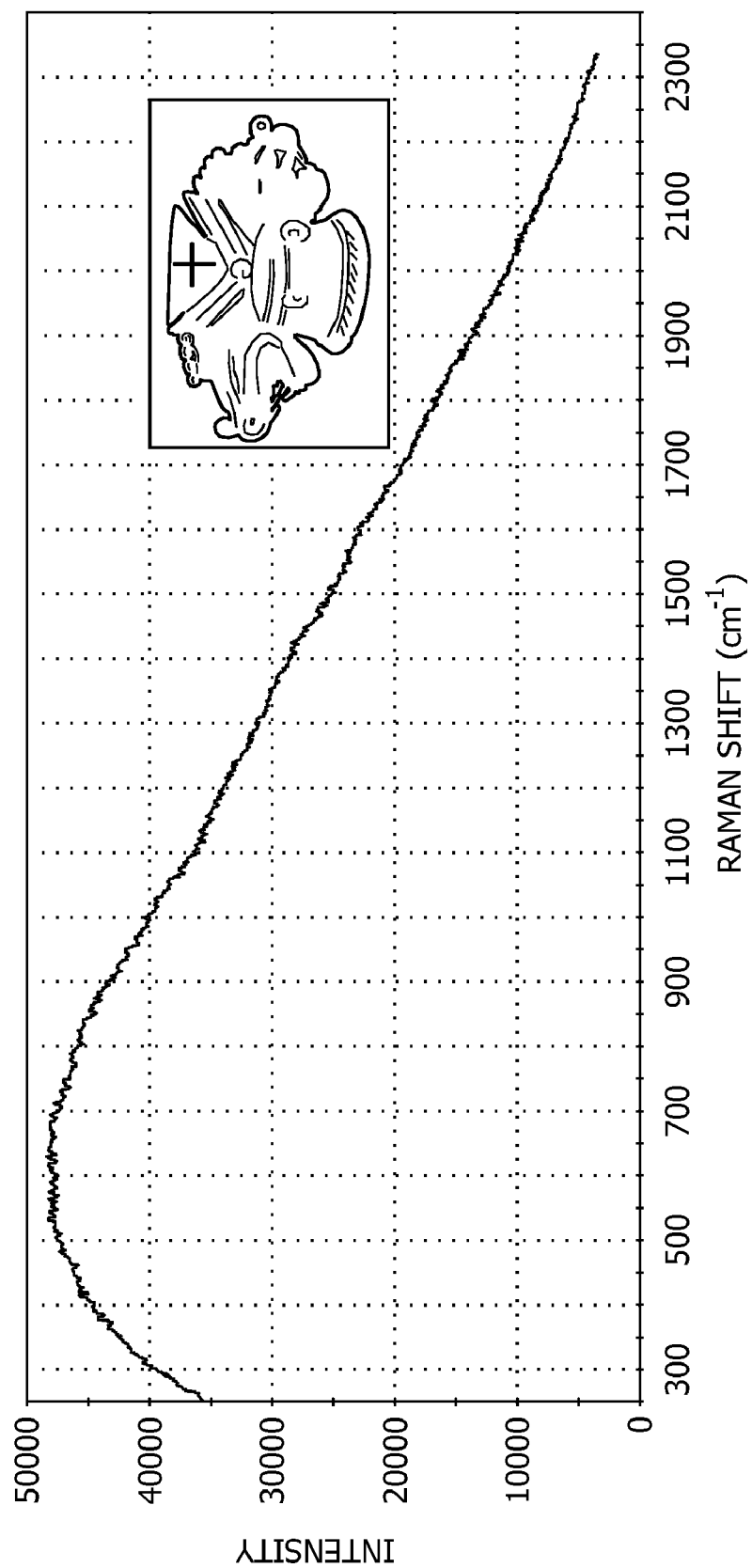
Figure 8D:
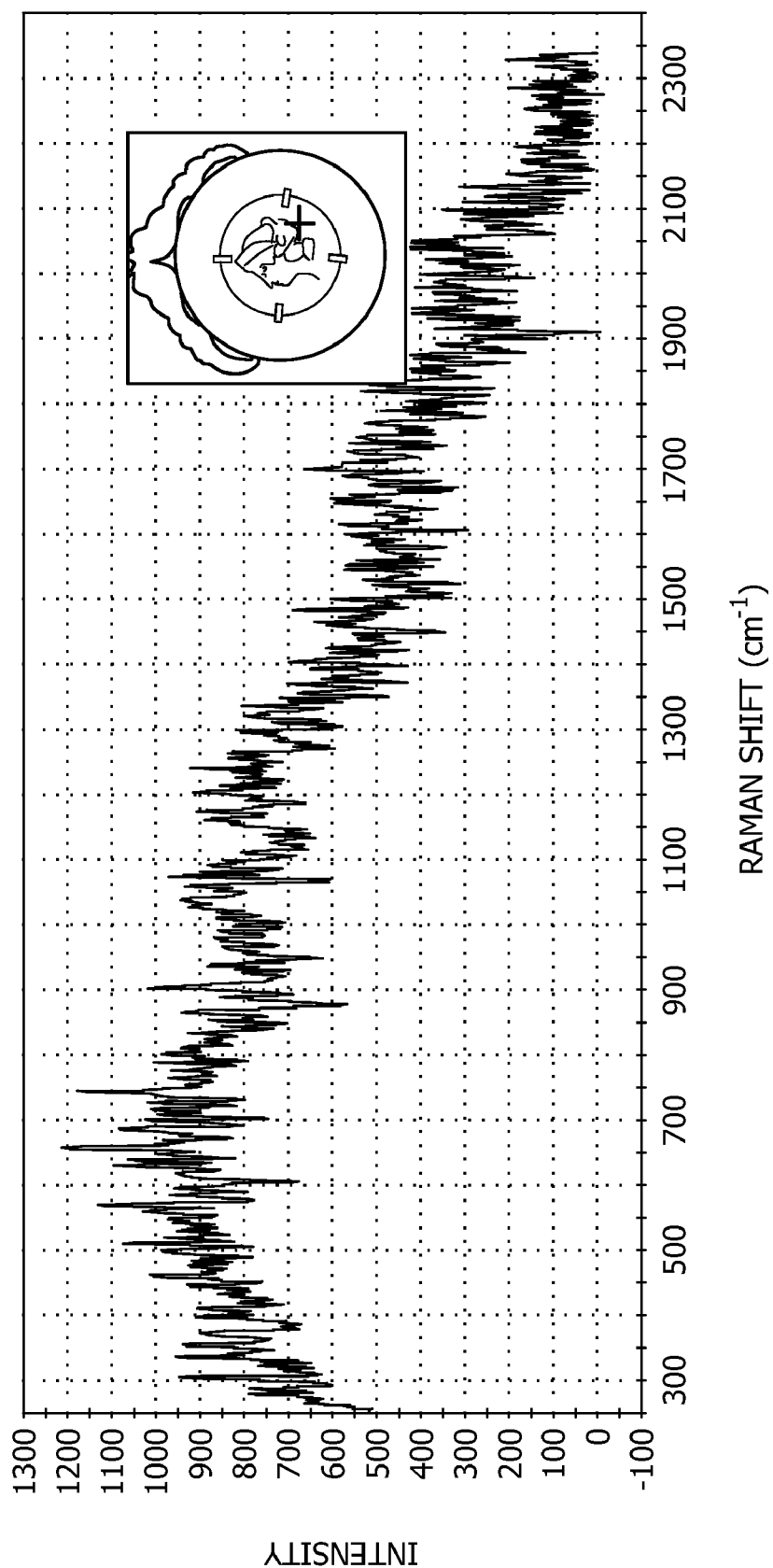

Referring to FIG. 7, experiment 7 comprised laser scans of pre-Columbian sculptures made of Mexican Tecali which is an Onyx marble and is a silica included polycrystalline limestone found in caves in the village of Tecali, Mexico. Three artifacts were tested against a modern ash tray (est. age: 50 BP). The artifacts were two Teotihuacan culture stone masks, one which was proto Olmec cultural phase (est. age: 1800-2300 BP) and the other a Teotihuacan IV (est. age: 1350-1500 BP). The third artifact was a classic Teotihuacan IV Mask of Central American Mayan trade from Tecali from Mexico. The 785 nm laser was operated at 50 mw and 1 integration. These tests were ran against a modern made Tecali tourist item from Mexico estimated to be 50-70 BP from an art deco period. The overlay graph indicates high fluorescence and a high degree of relative antiquity of the artifacts with respect to the low fluorescence observed on from the ash tray, a modern tourist item.

Experiment 8

Referring to FIGS. 8A-8D, experiment 8 tested Gold, symbol Au, which is one of the Noble Metals of the Chemical periodic table of elements. The laser system was set at 25 mw power and 10 integrations. Three pre-Columbian gold pieces were tested which comprised a Columbian Calima culture gold ring (est. age: 1000-1500 BP), a Panamanian Code embossed gold Pectoral (est. age: 900-1000 BP), and a Panamanian Code Bell (est. age: 900-1000 BP). The artifacts were tested against a 1904 U.S. 20 dollar gold piece minted in Philadelphia. The results showed a high relative fluorescence from the pre-Columbian gold artifacts, which indicated a high degree of antiquity or age of the artifacts with respect to the modern 20 dollar gold piece. Note the high fluorescence peak at around 850 intensity and 600 cm--1 from the 20 dollar coin in FIG. 8D.

Experiment 9

Figure 9:
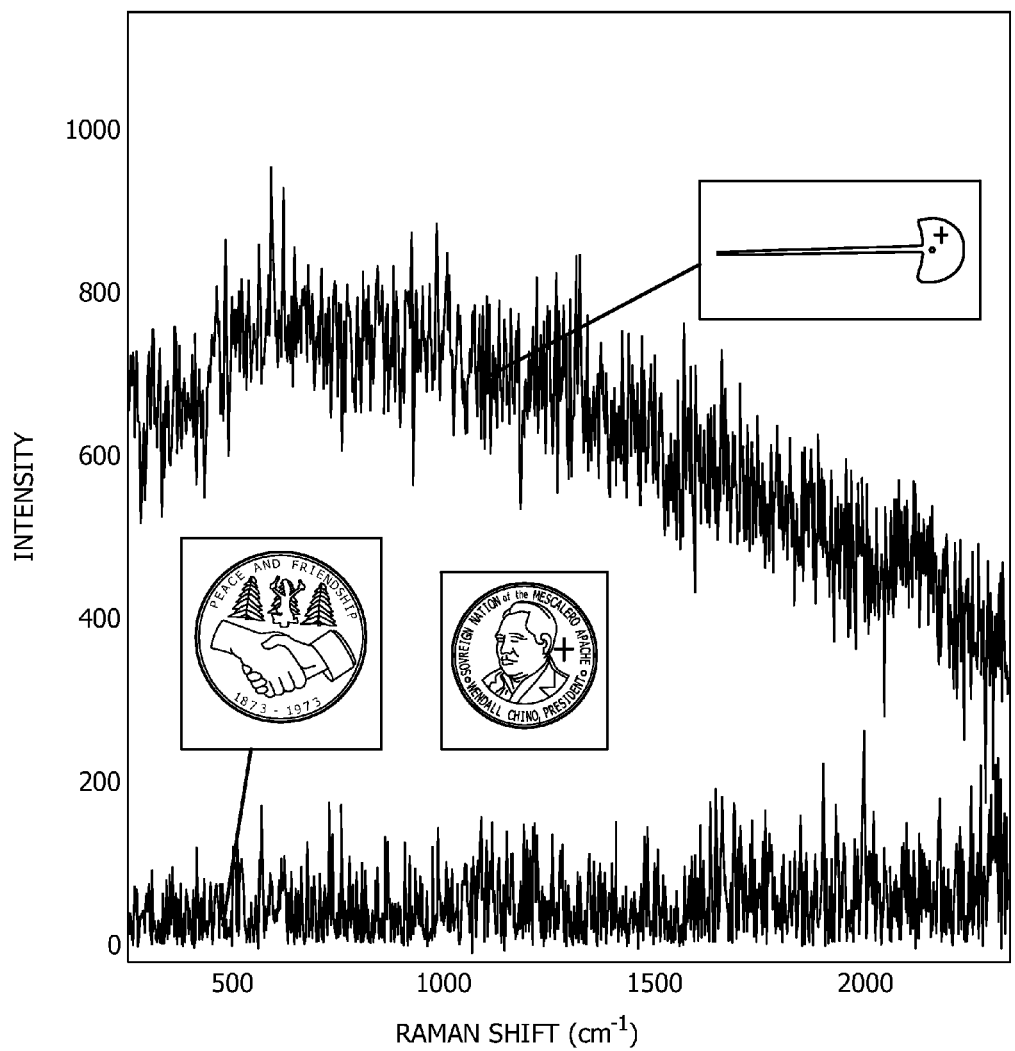
FIG. 9 is an illustration of the fluorescence measured from an antique and a modern silver artifact.

Referring to FIG. 9, experiment 9 tested a silver artifact. Two items tested were a pre-Columbian silver Tupu or clothespin from South America and a 1973 minted 10 oz silver Reverse Peace medal from the Mescalero Apache commemorating a centennial event. The Tupu showed a fluorescence peak at 750 intensity at around 700 cm--1 and the Peace medal showed low fluorescence at around 35-40 intensity at 500 cm--1. Thus, the large fluorescence seen on the Tupu indicates a high relative age or antiquity of the Tupu artifact.

Experiments 10-12

Figure 13:
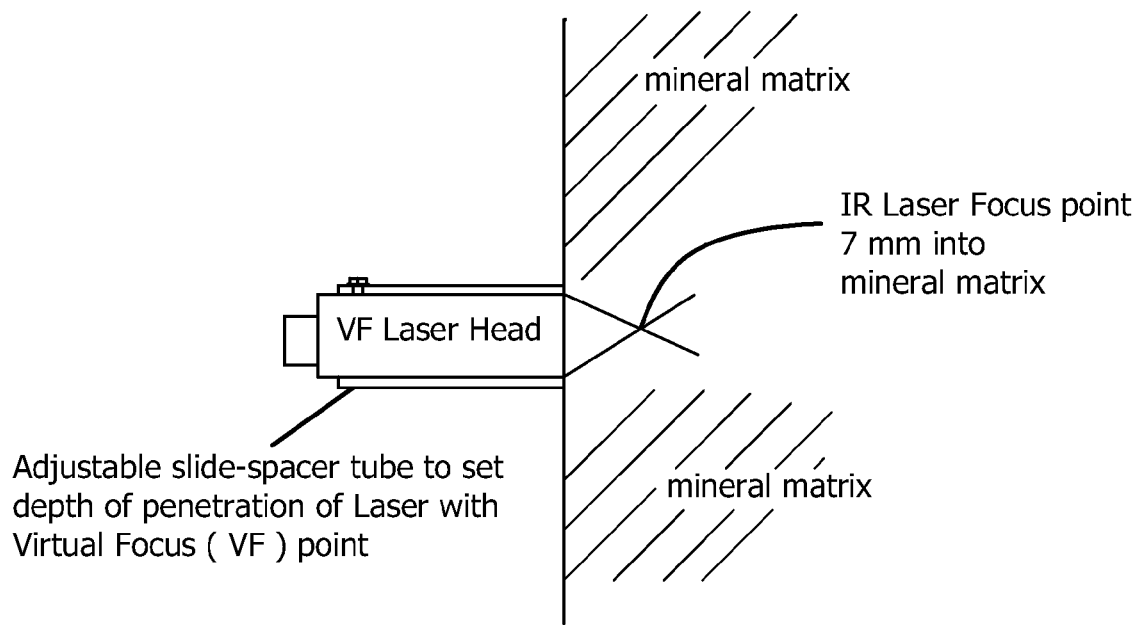
FIG. 13 is a diagram of an set up of a laser having a virtual focus head for irradiating below a surface of an artifact.

In a further embodiment of the method, the artifact in question is used as its own reference to determine whether markings, engravings, etchings or similar features are authentic or created when the artifact as a whole was created. Referring to FIG. 13, a reference measurement of the fluorescence after laser stimulation is measured by focusing a laser at a depth in the artifact, away from the majority of the radiation damage that results in the patina. One would expect a similar response between the spectrograph of the reference measurement and a measurement of the fluorescence from the artifact stimulated at the surface of a relatively recent etching.

When taking measurements of the fluorescence at depth, one must account for the attenuation of the laser light and the fluorescence through depth of the material of the artifact. In one embodiment, the method may account for the attenuation by increasing the integration time of the spectrometer for reference measurements relative to the surface measurements of etchings. In one embodiment, the integration time may be determined from the attenuation coefficient of the laser light through the material.

The attenuation coefficient of a material may be determined by a transmission experiment of the laser light through a known thickness of material and using the formula $T=e^{-at}$ where T=transmittance, a=attenuation coefficient, t=material thickness, e=naperian log. By measuring the intensity of the transmitted laser light through air and for the laser light after traveling through a known thickness of material and taking the ratio, and then solving for the attenuation coefficient.

Figure 14:
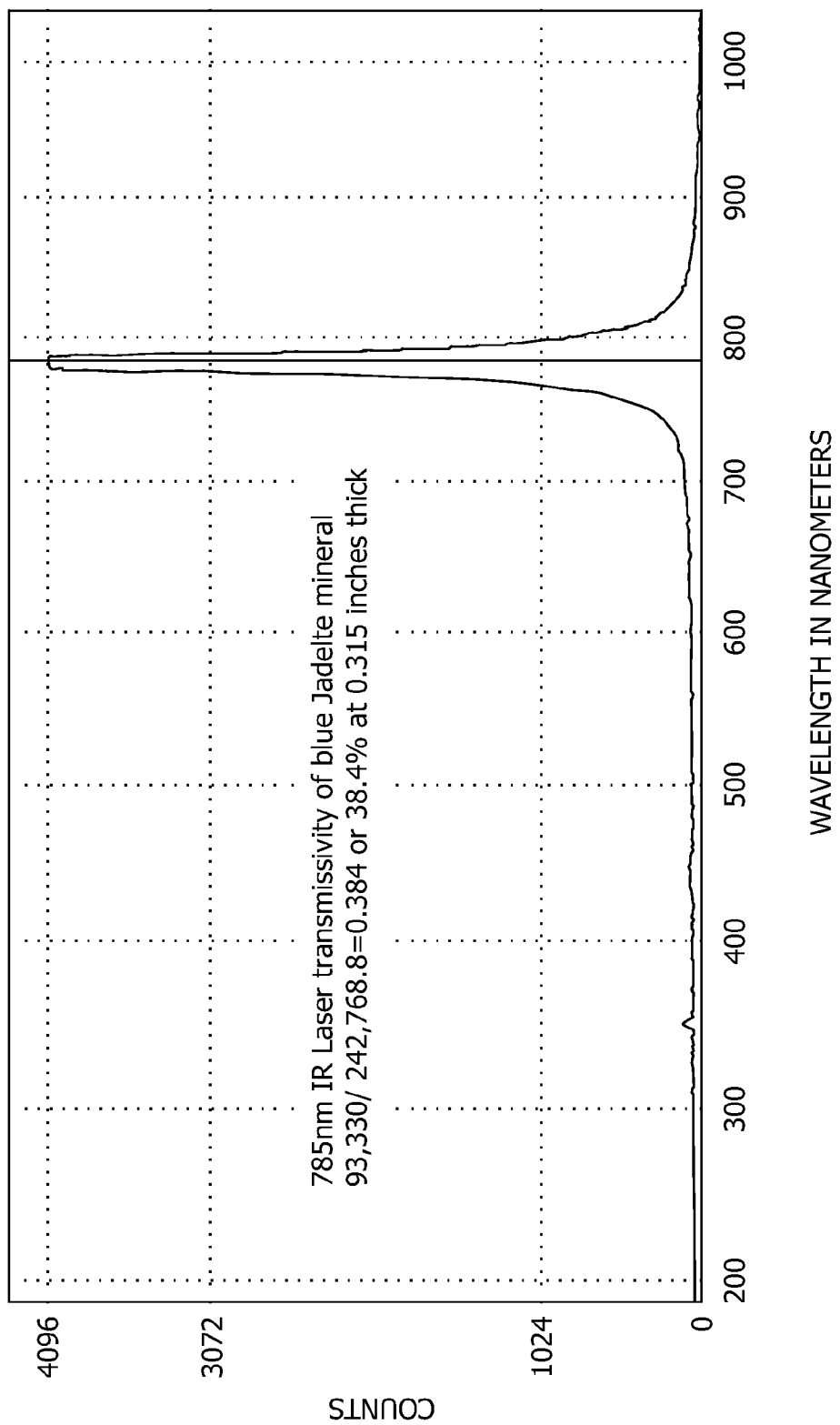
FIG. 14 is an illustration of a fluorescence curve for a transitivity experiment.

In another embodiment, the integration time for measuring the fluorescence for the laser focused at depth d in the artifact may be determined a transmission determination. A typical transmission result is shown in FIG. 14. In a transmission determination, the intensity of the light laser light after traveling through a thickness d of material is divided into the measured intensity of the laser light through air. This ratio of transmissions is multiplied by 2 to determine the factor by which the integration time is increased, to account for the fact that the laser light is attenuated traveling to the depth d and the fluorescence is attenuated traveling out of the material from the depth d to the spectrometer. If the depth d is different that the thickness of material used in the transmission determination, one can adjust the ratio of transmissions by multiplying by a suitable ratio of d1 and d2 where d1 is the depth in the artifact where the laser is focused and d2 is the thickness of the artifact material used in the transmission experiments.

In still another embodiment, the method comprises measuring the fluorescence of the material due to laser light stimulation focused at a depth d inside the material, and adjusting the integration time of the spectrometer until the reading on the spectrometer matches a fluorescence reading from laser stimulation at the surface.

Figure 10:
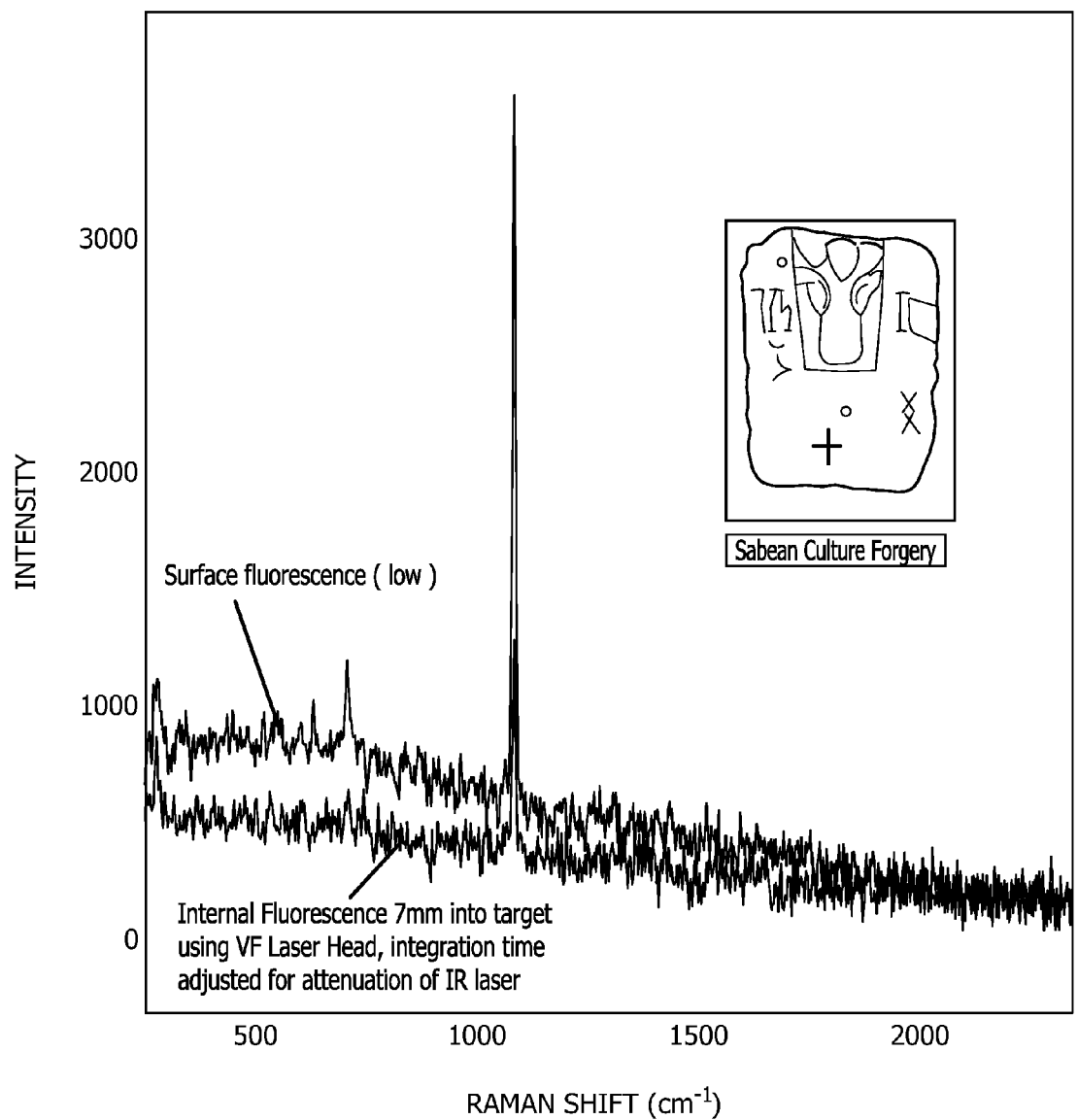
FIG. 10 is an illustration of the fluorescence measured from the surface of a Sabean culture artifact and from fluorescence stimulated from a laser focused 7 mm beneath the surface.

Referring to FIG. 10, experiment 10 tested a Sabean culture alabaster panel from the South Arabian zone. A surface scan (laser stimulation at the surface and subsequent reading of the fluorescence) was performed as well as a scan 7 mm into the artifact. Based on the similarity of the results of the two fluorescence curves, one can conclude that the artifact was constructed relatively recently.

Figure 11:
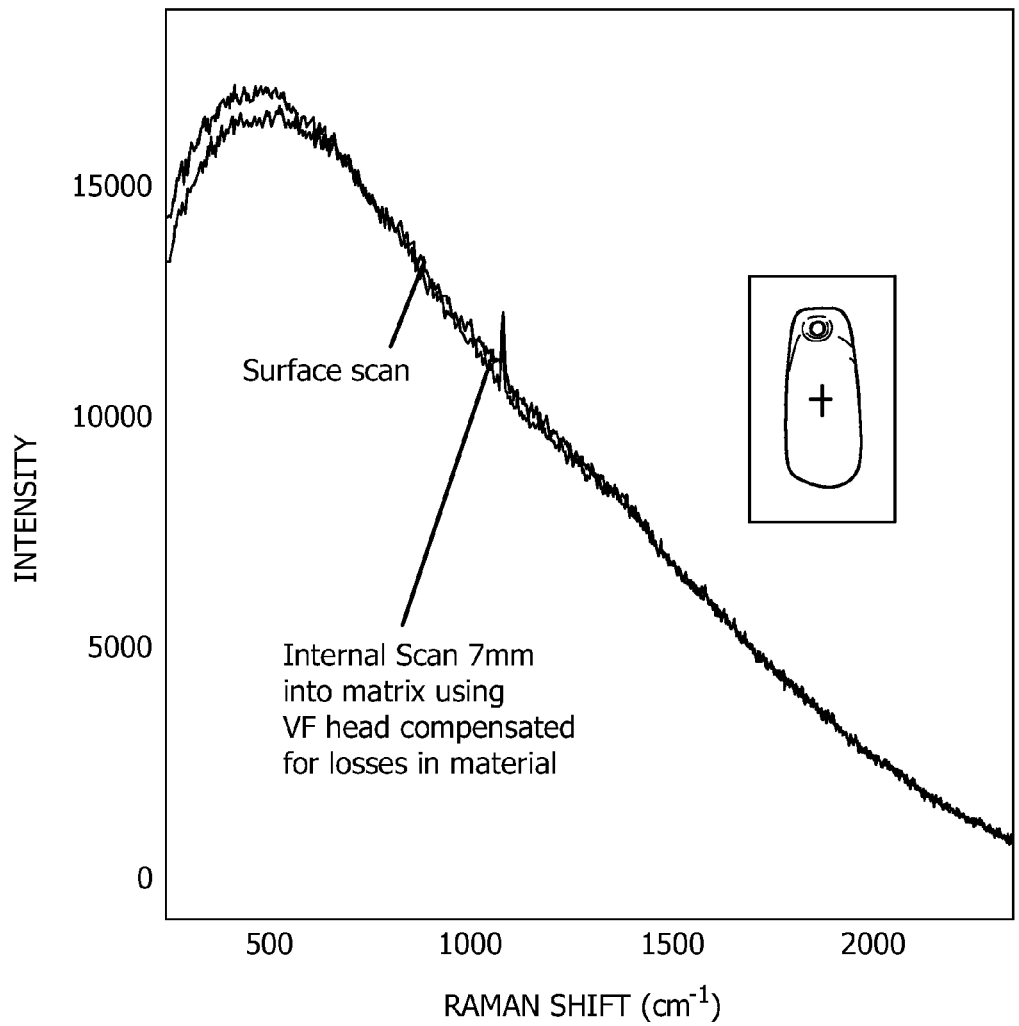
FIG. 11 is an illustration of the fluorescence measured from the surface of an ancient artifact and from fluorescence stimulated from a laser focused 7 mm beneath the surface.

Referring to FIG. 11, experiment 11 tested a fossiliferrious marble artifact purportedly from the Chinese Neolithic period. Experiment 11 conducted a surface scan and compared it to an internal scan 7 mm into the artifact using a virtual focus head and using a technique for compensating for the attenuation of light through the artifact. Based on the similarity of the fluorescence, one can conclude that this artifact is a forgery.

Figure 12:
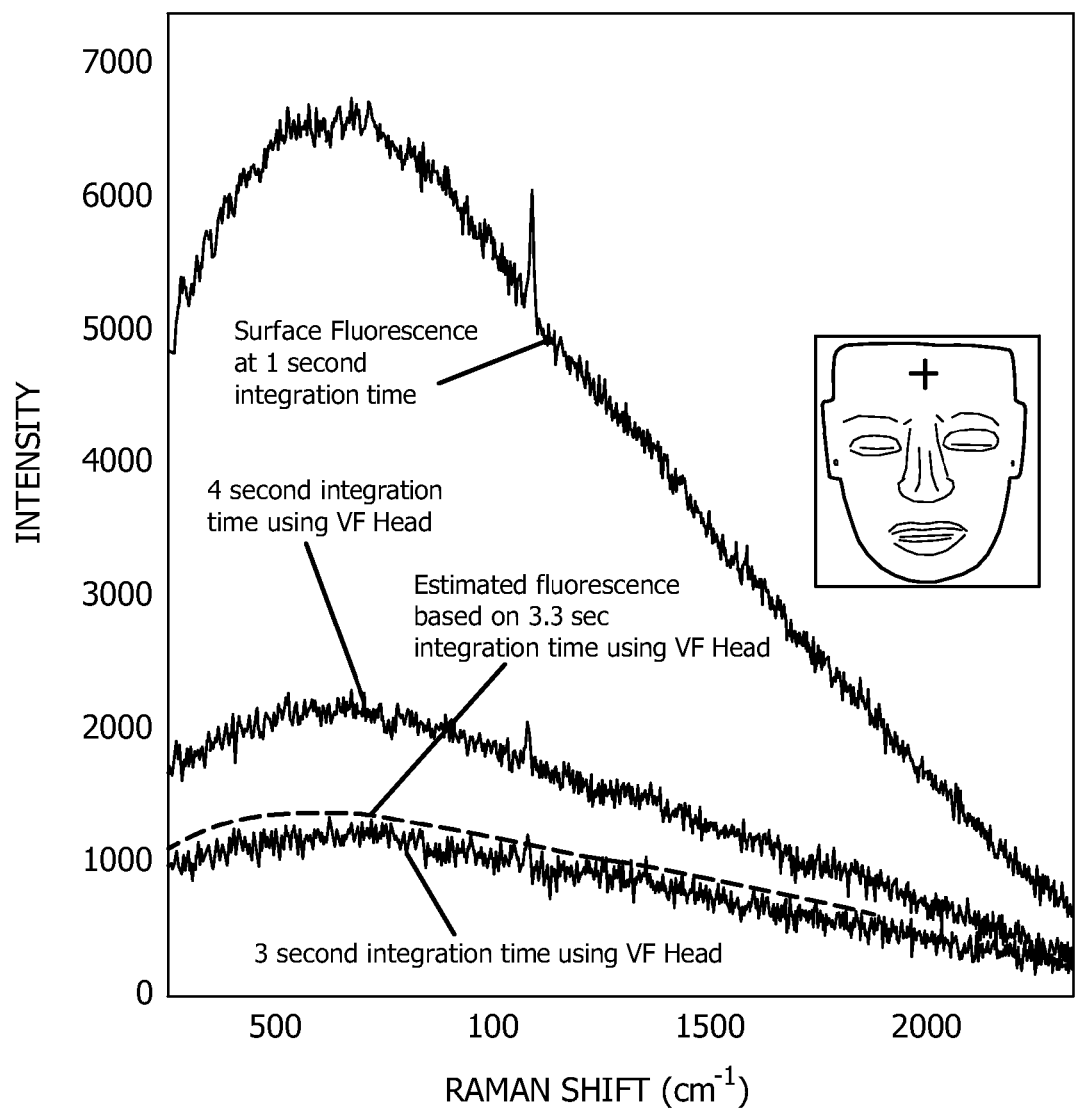
FIG. 12 is an illustration of the fluorescence measured from the surface of an ancient artifact and from fluorescence stimulated from a laser focused 7 mm beneath the surface.

Referring to FIG. 12, experiment 12 tested a Mexican Tecali Pre-Columbian Teotihuacan culture face panel. A 785 nm laser was used to irradiate both the surface and a depth of 7 mm below the surface. A full contact head was used for the surface scan and the virtual focus head was used from the scan at 7 mm. The integration time for the surface scan was 1 second, while the integration time for the 7 mm scan was conducted at 3 second and 4 second integration times respectively, since the equipment used in this experiment could not be set to an integration time of 3.3 seconds.

An integration time of 3.3 seconds was determined by using a method of taking the value of the laser light intensity through air and dividing it into the intensity of the laser light after penetrating through 9 mm of artifact material. This number was multiplied by the ratio of 7 mm/9 mm and the inverse of the result was computed. This was then multiplied by a factor of 2 to account for attenuation of the laser light penetrating to the 7 mm depth and for attenuation of the fluorescence light traveling from 7 mm to the surface where it is read by the spectrometer.

A curve for a 3.3 second integration time for the scan conducted at the 7 mm depth was interpolated using the 3 and 4 second curves. Since the surface scan exhibited a 3-5 times increase in fluorescence over the 7 mm scan, one can conclude that the artifact is not a forgery based on the disparities of the curves.

Figure 15:
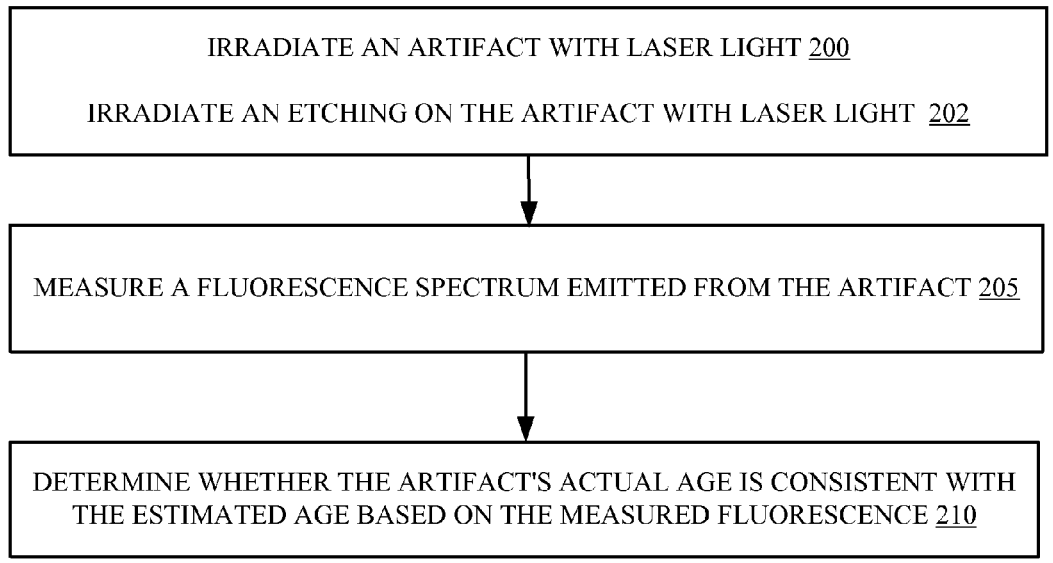
FIG. 15 is a flow chart of a method of authentication in accordance with the principles of the invention.

Referring to FIG. 15, a method for authenticating an estimated age of an archaeological artifact comprises: in a step 200, irradiating the artifact with laser light; in a step 205 measuring a fluorescence spectrum emitted from the artifact; and in a step 210 determining whether the artifact's actual age is consistent with the estimated age based on the measured fluorescence. In one embodiment, the method of authentication may further comprise in a step 202 irradiating an etching on the artifact with laser light. The term artifact may refer to an entire artifact as a whole or a particular feature of interest on an artifact such as an engraving, etching or writing.

Figure 16:
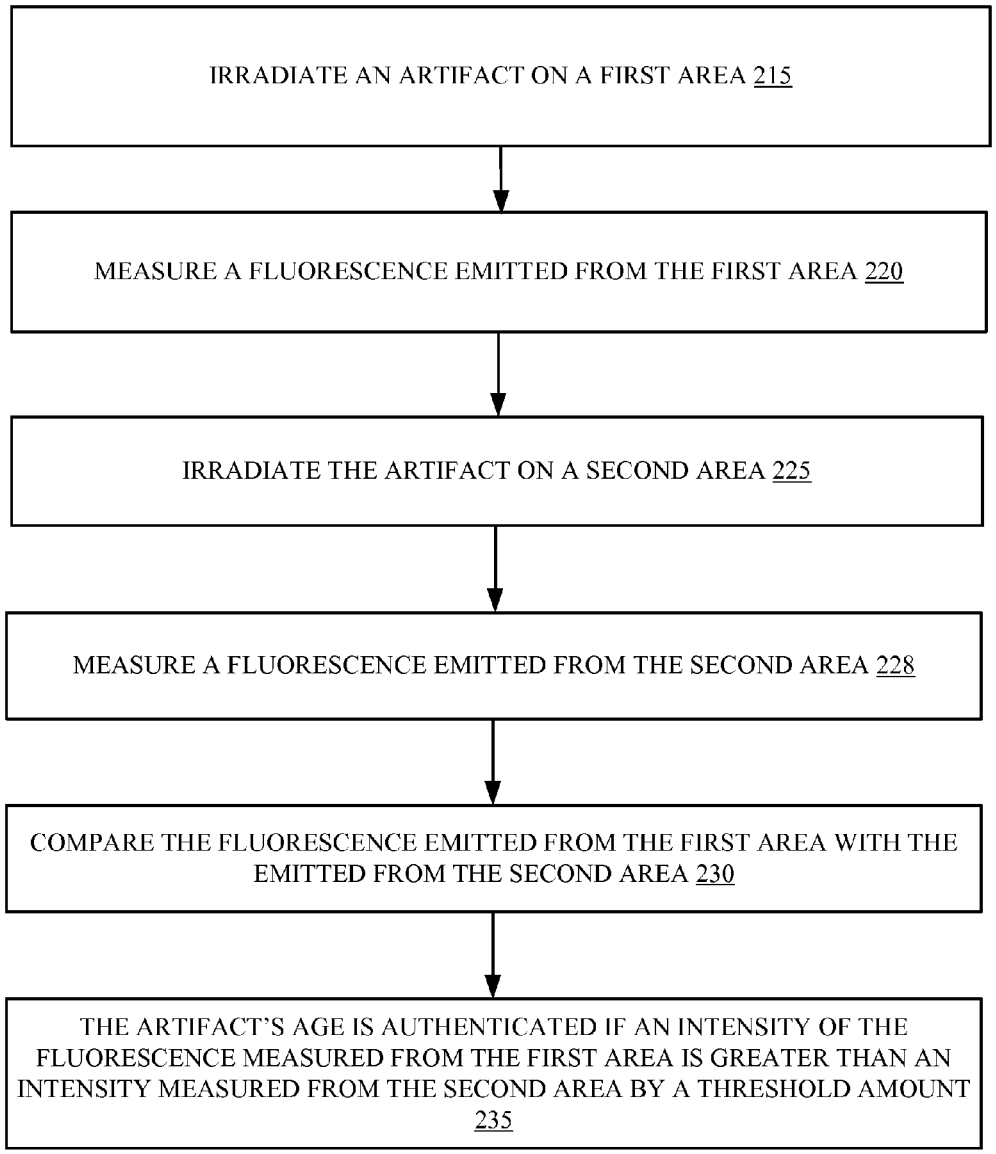
FIG. 16 is a flow chart of a method of authentication in accordance with the principles of the invention.

In a variant, referring to FIG. 16, the method of authentication of may comprise: in a step 215 irradiating the artifact on a first area; in a step 220 measuring a fluorescence emitted from the first area; in a step 225 irradiating the artifact on a second area; in a step 228 measuring a fluorescence emitted from the second area; and in a step 230 comparing the fluorescence emitted from the first area with the emitted from the second area. In a step 235, the artifact's age is authenticated if an intensity of the fluorescence measured from the first area is greater than an intensity measured from the second area by a threshold amount. Threshold amounts discussed in this document may be selected by the operator of the method to suit the operator's degree of confidence. In the method above, for example, the operator may be willing to accept less certainty in the authentication and thus a smaller difference in the intensities to determine whether the artifact is authentic.

In one embodiment, the first area comprises a top surface layer of the artifact and the second area comprises a top surface layer of the artifact having been damaged by removal of part of the surface. The method may comprise removing a portion of the surface of the artifact.

Figure 17:
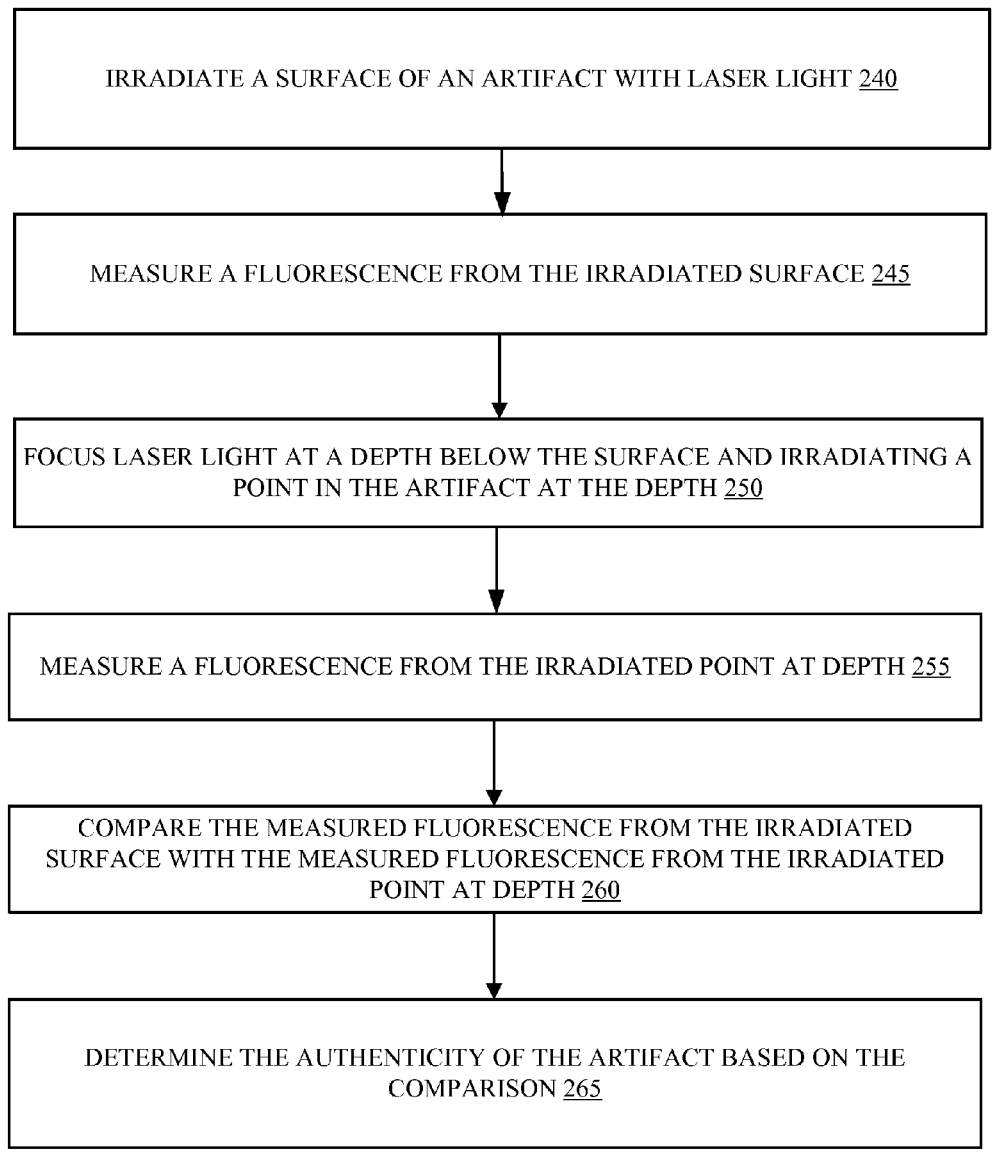
FIG. 17 is a flow chart of a method of authentication in accordance with the principles of the invention.

In a further variant, referring to FIG. 17, the method of authentication may comprise: in a step 240 irradiating a surface of the artifact with laser light; in a step 245 measuring a fluorescence from the irradiated surface; in a step 250 focusing laser light at a depth below the surface and irradiating a point in the artifact at the depth; in a step 255 measuring a fluorescence from the irradiated point at depth; in a step 260 comparing the measured fluorescence from the irradiated surface with the measured fluorescence from the irradiated point at depth; and in a step 265 determining the authenticity of the artifact based on the comparison.

Figure 18:
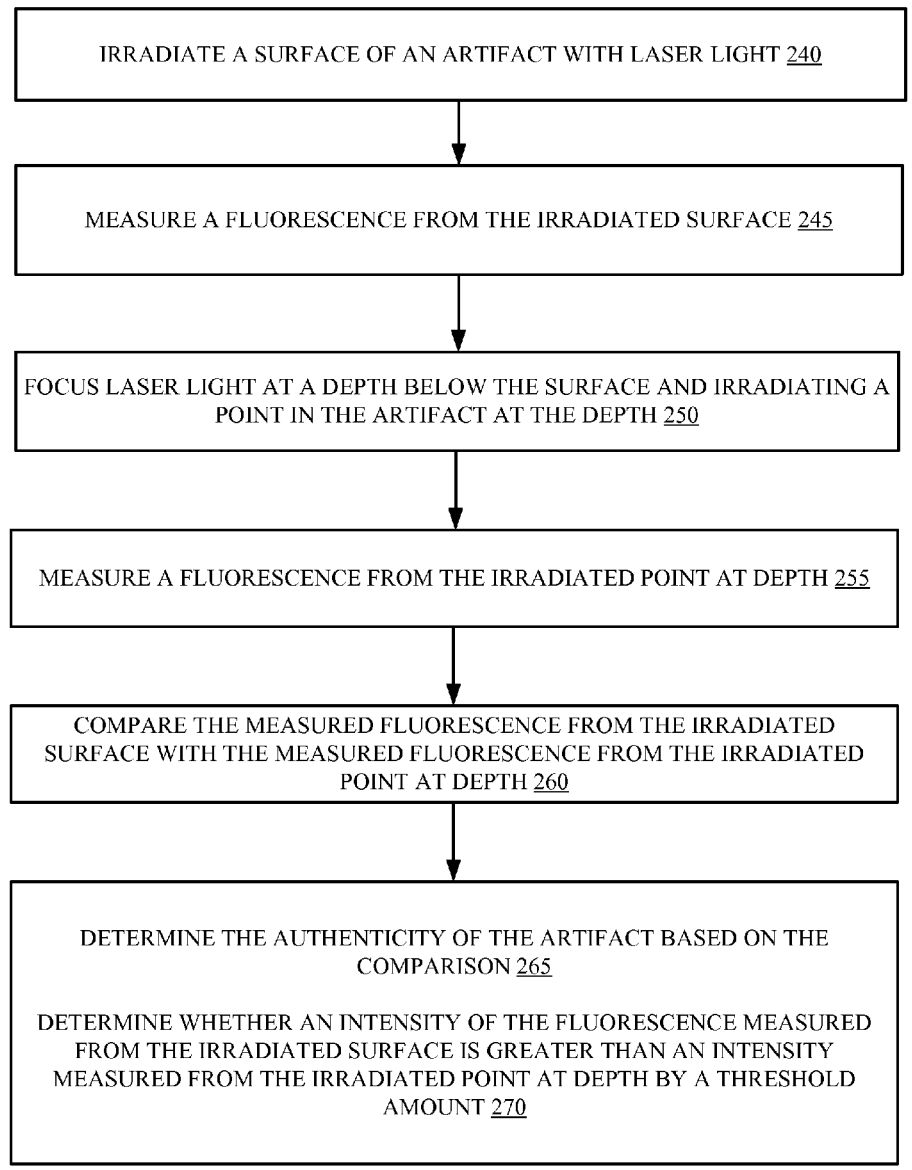
FIG. 18 is a flow chart of a method of authentication in accordance with the principles of the invention.

In still another variant, referring to FIG. 18, determining the authenticity of the artifact based on the comparison comprises determining in a step 270 whether an intensity of the fluorescence measured from the irradiated surface is greater than an intensity measured from the irradiated point at depth by a threshold amount.

Figure 19:
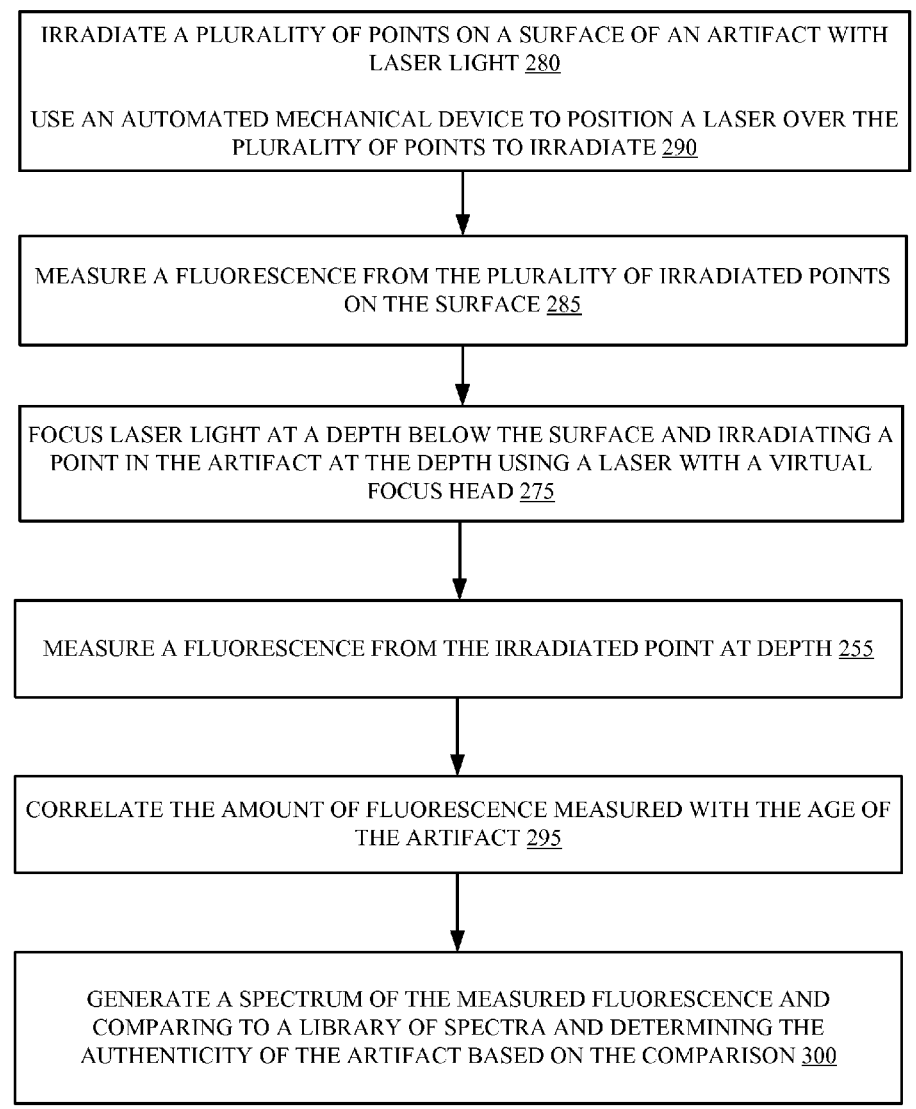
FIG. 19 is a flow chart of a method of authentication in accordance with the principles of the invention.

In yet a further variant, referring to FIG. 19, the method may comprise in a step 275 using a virtual focus head laser to irradiate the point at depth and using a full contact head laser to irradiate a surface.

In another variant, referring to FIG. 19, the method may comprise in a step 280 irradiating a plurality of points on the surface of the artifact and in a step 285 measuring the fluorescence from the plurality of points on the surface. In one embodiment, the method may comprise in a step 290 using an automated mechanical device to position a laser over the plurality of points to irradiate, for example, a robot.

In a further variant, referring to FIG. 19, the method may include in a step 295 correlating the amount of fluorescence measured with the age of the artifact, wherein the artifact is of human origin. In one embodiment, in a step 300 correlating the amount of fluorescence measured with the age of the artifact comprises generating a spectrum of the measured fluorescence and comparing to a library of spectra and determining the authenticity of the artifact based on the comparison.

Figure 20:
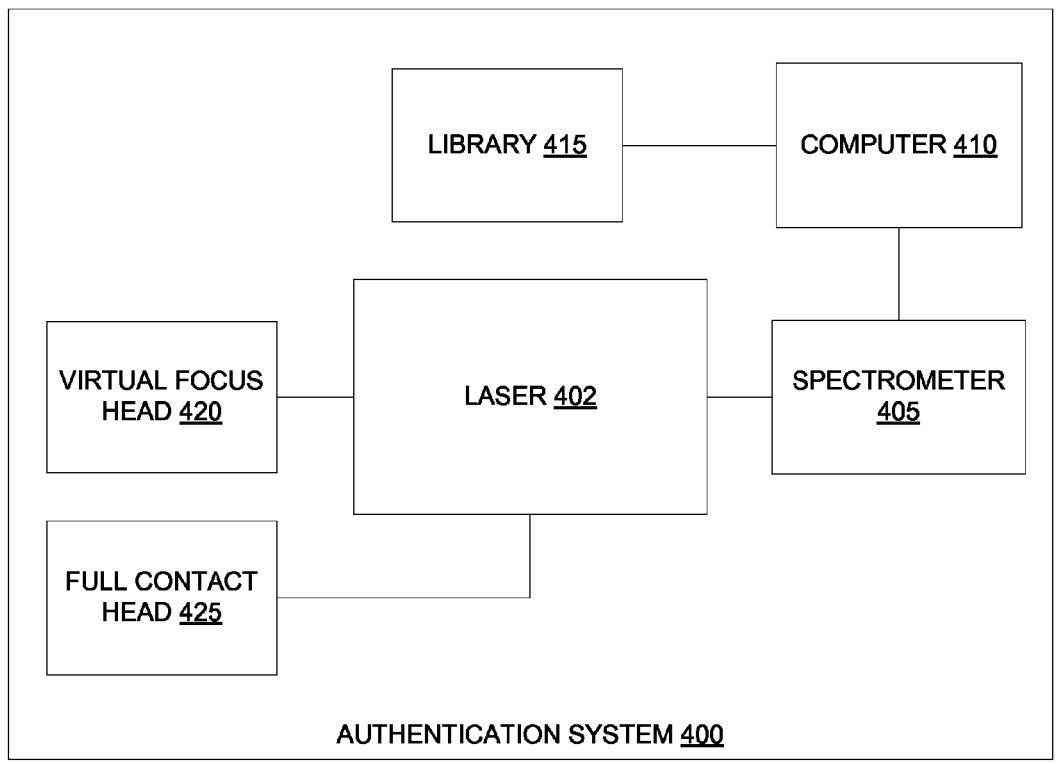
FIG. 20 is a block diagram of a system of authenticating the age of an artifact.

In still another variant, referring to FIG. 20, an authentication system 400 for debunking a purported age of an artifact comprises: a laser 402; a spectrometer 405 configured for measuring fluorescence stimulated by laser light absorption of the artifact; and a computer 410 configured to analyze the fluorescence measured by the spectrometer and determine whether the fluorescence measured meets a threshold amount. The computer is configured to display whether the fluorescence measured meets a threshold amount and wherein the purported age of the artifact is debunked if the measured fluorescence does not meet the threshold amount. In one embodiment, the laser emits light having 785 nanometer wavelengths.

In yet a further variant, the threshold amount is determined from a library 415 of spectra from laser stimulated material of known approximate age ranges and compositions. In one embodiment, the system comprises a laser having virtual focus head 420 and a laser having full contact head 425.

Figure 21:
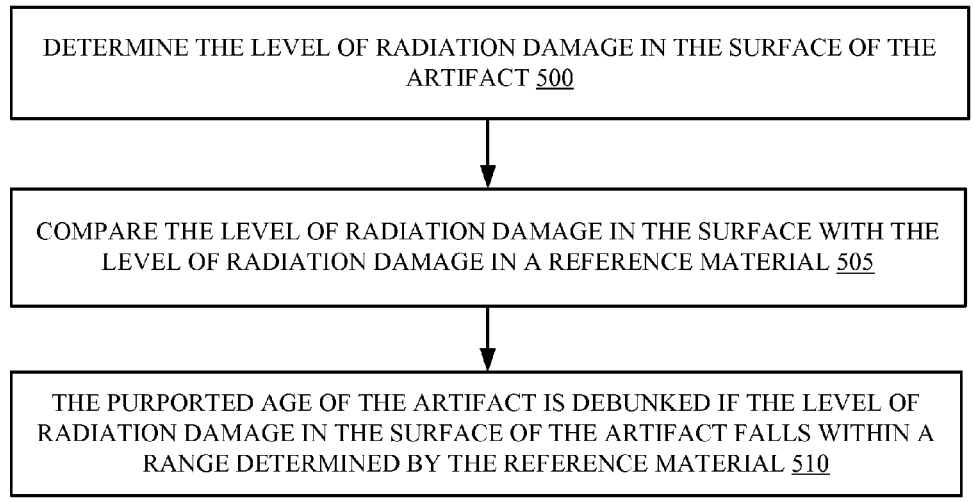
FIG. 21 is a flow chart of a method of debunking a purported age of an artifact in accordance with the principles of the invention.

In another variant, referring to FIG. 21, a method for debunking a purported age of an artifact comprises in a step 500 determining the level of radiation damage in the surface of the artifact and in a step 505 comparing the level of radiation damage in the surface with the level of radiation damage in a reference material. In a step 510, the purported age of the artifact is debunked if the level of radiation damage in the surface of the artifact falls within a range determined by the reference material.

Figure 22:
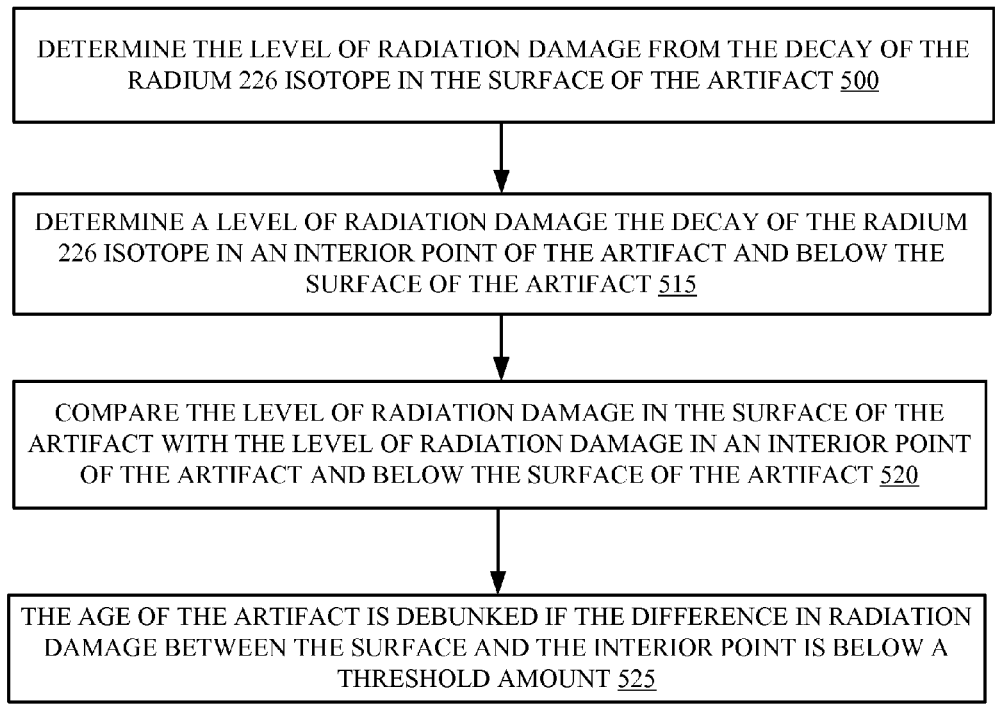
FIG. 22 is a flow chart of a method of debunking a purported age of an artifact in accordance with the principles of the invention.

In a further variant of the method for debunking the age of an artifact, referring to FIG. 22, the reference material comprises the artifact itself, and the method further comprises in a step 515 determining a level of radiation damage in an interior point of the artifact and below the surface of the artifact and in a step 520 comparing the level of radiation damage in the surface of the artifact with the level of radiation damage in an interior point of the artifact and below the surface of the artifact. In a step 525, the age of the artifact is debunked if the difference in radiation damage between the surface and the interior point is below a threshold amount. In one embodiment, the method determines the level of radiation damage in the surface of the artifact caused by the decay of the Radium 226 isotope. In a further variant, the method comprises detecting a patina of radiation damage on the surface of the artifact.

Application of pulsed laser tests in the method of the present invention

The method of the present invention can further be utilized to simulate a thermoluminescence (TL) test on an artifact comprising certain heat treated minerals and clays, such as for example low to high fired ceramics, terra cottas, and pyrolized jades.

The laser is set up in a pulsed mode normal to the surface of a target to be tested and fired at a repetition rate and energy density sufficient to cause heating of the target to temperatures in the range of between 100 degrees F. and 900 degrees F. and preferably in the range to not exceed thermal stresses in the target to cause damage by spall or fracturing. In one embodiment, the method of the present invention provides a non-destructive test which is indifferent to modern TL techniques where a small sample has to be removed from the target by drilling, which causes damage to the value of an artifact. The TL method is basically time consuming and costly. It takes about one month minimum time and at the time of this writing, $750-$1000 dollars for the test. The present method overcomes these deficiencies by providing a real time test in one or two minutes as well as no damage to the target which has to ultimately be restored in the sampled area at additional cost.

A more detailed description of the pulsed mode laser test comprises tracking of the fluorescence (glow) as well as the dynamic rate of change of the fluorescence w.r.t. to time/number of pulses/second, etc and also tracking this w.r.t. a specific wave number (cm--1). Therefore, in view of this, the x-y axis of a 2-D plot will show fluorescence versus number of pulses. This function is recorded at a constant wave number value. Choosing the correct wave number value to track w.r.t. to material tested varies as some materials have higher fluorescence maximums at different wave numbers. An example is terracotta material's wave number can be in the range of 250-1500 cm--1 and more specifically in the range of 500-1300 cm--1. To determine this, a single pulse is fired into the target and the fluorescence maxima at the specific wave number is observed. Then the system is set up in a pulsed mode to track the fluorescence/time at this constant wave number. An example to this is a typical buff terracotta might have a maximum fluorescence at 700 cm--1, whereas a dark black carbonaceous terracotta might have maxima fluorescence around 1400 cm--1. In the pulsed mode, a typical pulse width can be set from a range of 0.05 sec to about 1.5 sec and more specifically in the range of 0.10-1.0 sec. The pulse width determines the rate of heating of the target and has to be sufficient to overcome the thermal absorption and heat transfer and induced localized heating with a continuous positive temperature gradient with each pulse. Typical values are a pulse width of 0.4 sec, 300 mw power impinging on a 100 micron diameter area. At these settings a primary maximum of fluorescence can be seen in a few pulses and this drops off as the first nano trapped electrons are dumped from the 110 degrees C. trap. This 110 degrees C. trap is well known in the literature in TL testing. Further pulsing and target heating will cause secondary and sometimes tertiary maximums, such that, the final nano trapped electron population is fluxed out of the target. The math model describing the type of curve generated follows: e(−at)Cos(bt).

Choosing a good target area on a terracotta artifact.

Terracottas utilized by the ancients used a variety of compositions to achieve the desired mechanical properties of utilitarian pottery or ceremonial wares. Typical terracotta contains clays, feldspars, quartz grains, carbon, shell grit and the like. This distribution of components varies microscopically within the vessels surface, such that, it is desirable to line the laser beam up on a good spot to impinge on the specific components that react and produce fluorescence from laser heating. Materials rich in nano trapped electrons include quartz and feldspars, and therefore it is more desirable to place the laser in direct contact with these elements. Simply moving the laser from one spot to another in the pulsed mode to get a good dynamic fluorescence event can result from finding a "sweet spot" to test. Known good areas to test with a high percentage of sweet spots are areas of wear typically on the base, or adjacent thereto. The aid of a small jeweler's loupe or microscope can aid in quickly and easily placing the laser in a good spot for testing.

Experiment 13

Figure 23:
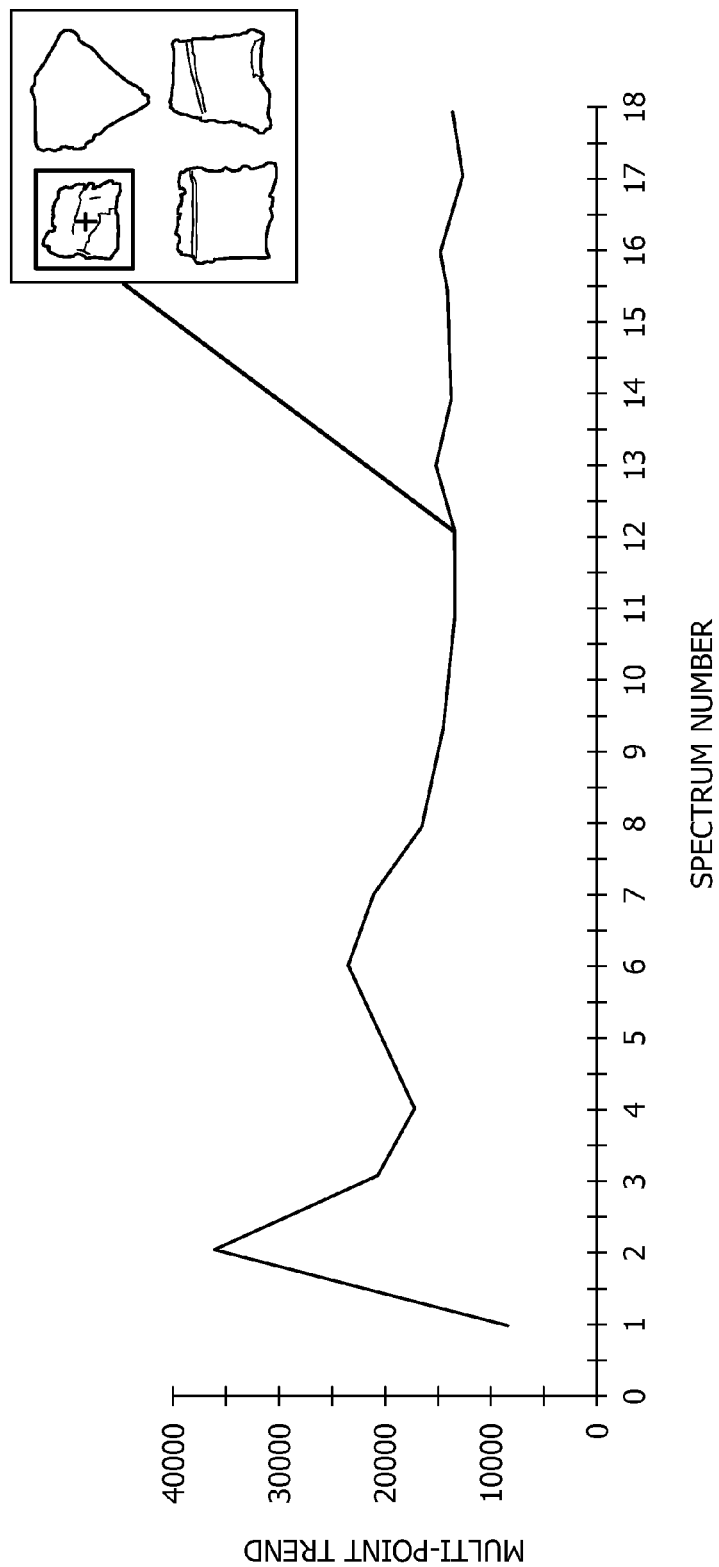
FIG. 23 is an illustration of the fluorescence measured from a Native American pottery shard in accordance with the method of the present invention.

Using Pulsed Laser to Produce Fluorescence in an Ancient Mississippian Period Pottery Shard Referring to FIG. 23, an ancient Native American pottery shard was procured for testing using the pulsed laser mode (IRSL) test. The spectrograph was saturated at 60,000 intensity such that the power was turned down to about 200 mw to get results. Thus, the test mode comprised 200 mw power, 0.40 sec pulse width, tracking @ constant 700 cm--1 on a Mississippian period pottery shard of age about 800-1000 years before present. The primary maximum can be seen after two pulses @ about 35K intensity and drops off to a new minimum at around 20K intensity. A secondary fluorescence maximum can be seen @ 6 pulses @ about 25K intensity and a third maxima can be seen after 13 pulses @ 15K intensity. This graph is completely analogous to a TL test.

Experiment 14

Figure 24:
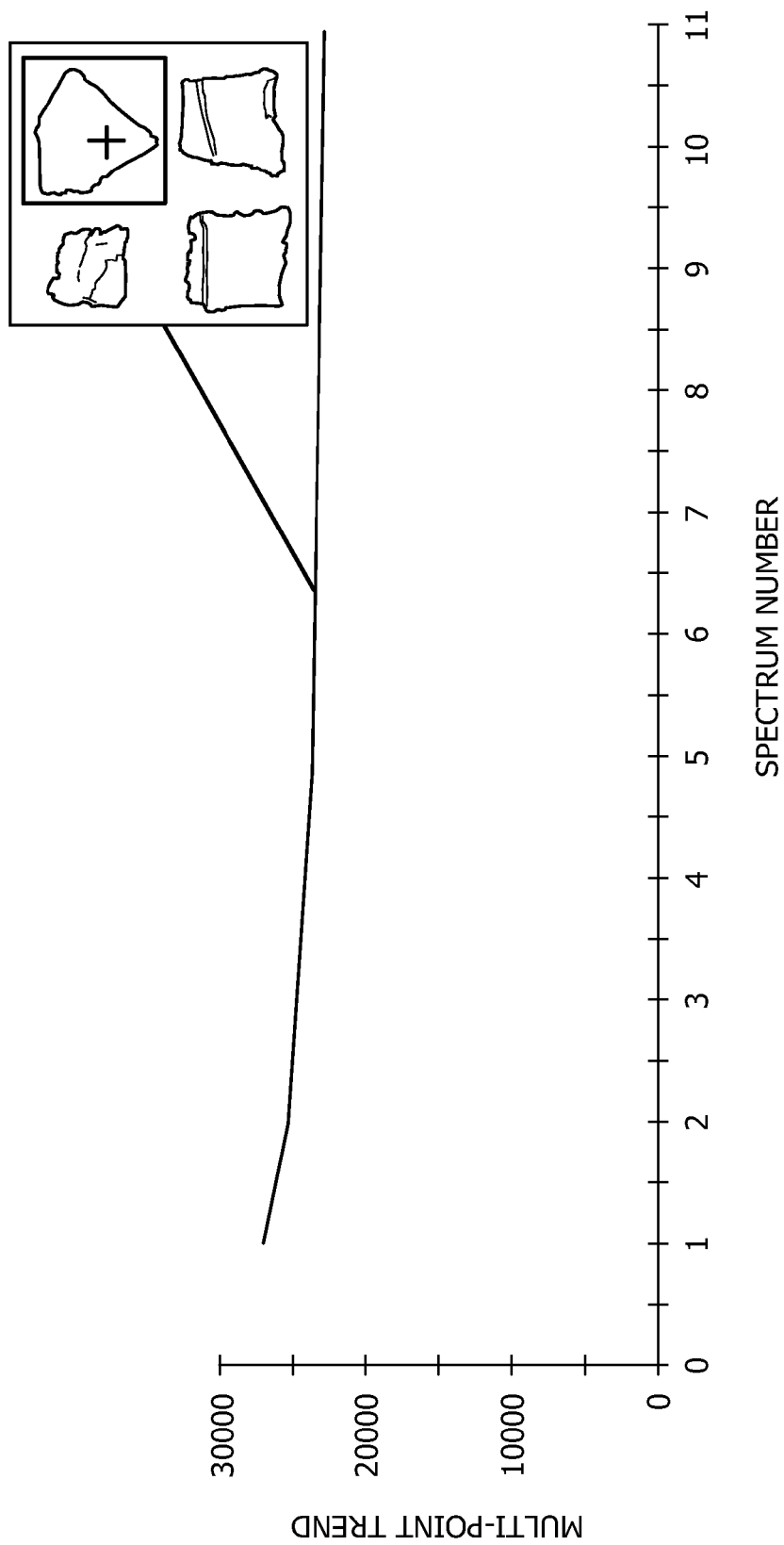
FIG. 24 is an illustration of the fluorescence measured from a Native American pottery shard having a fake purposed age in accordance with the method of the present invention.

Pulsed Laser Test Using a Post Heat Treated Mississippian Period Pot Shard to Verify the Quenching or Bleaching of the Population of Nano Trapped Electrons Referring to FIG. 24, a Mississippian pot shard was heat treated for 1 hour at 930 degrees F. Temperature was verified by using a calibrated IR thermometer gun rated to 1850 degrees F. The shard was cooled to room temperature before testing. Pulsed laser tests yielded a relatively flat line which indicates that most of the radiation induced electrons in the traps were liberated when the shard was treated with the background radiation while buried.

Experiment 15

Using a Fragment of a Pre-Columbian Vera Cruz Priest Comprising Terracotta

Figure 25:
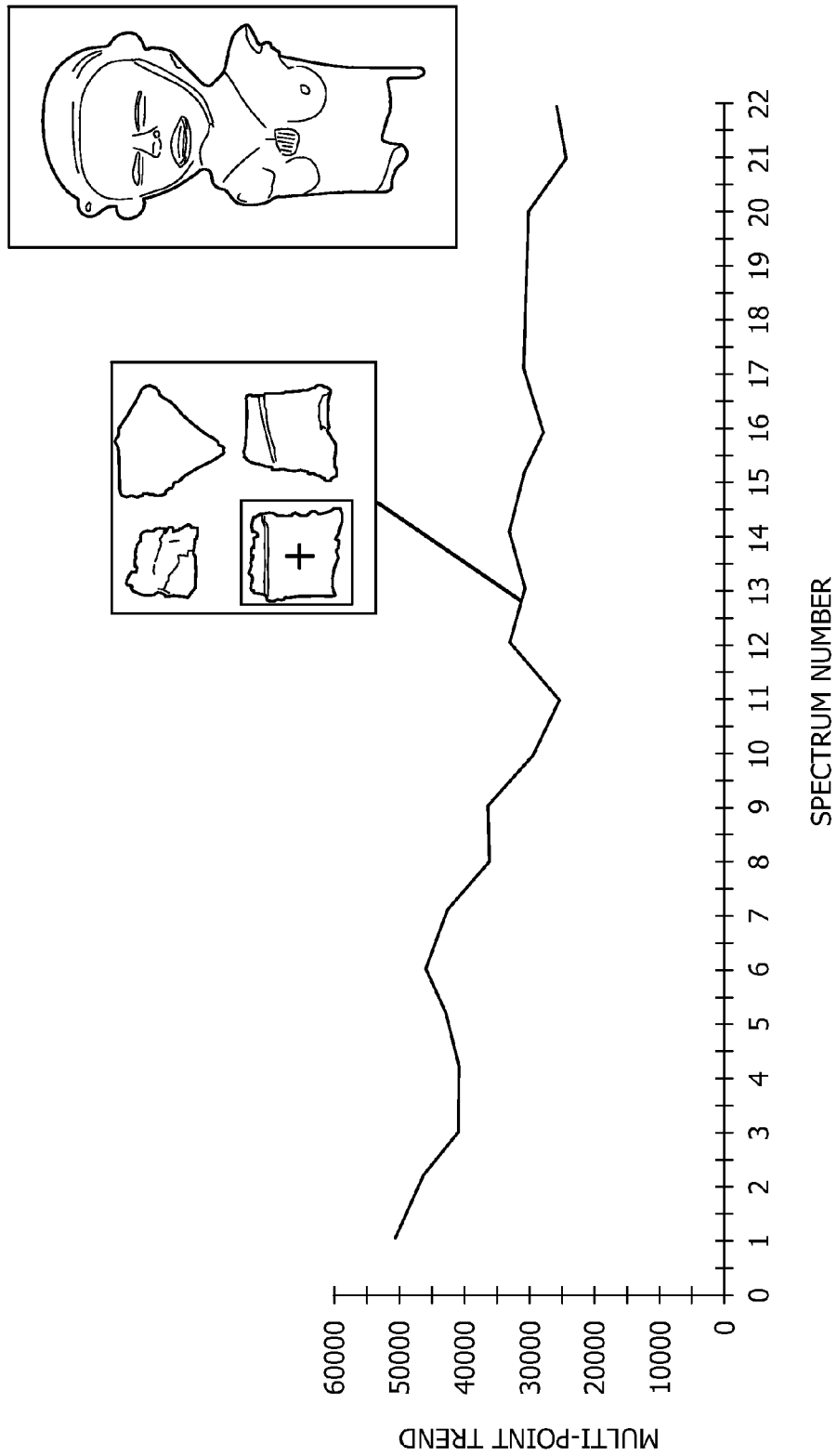
FIG. 25 is an illustration of the fluorescence measured from a non-heat treated pre-Columbian Vera Cruz priest fragment in accordance with the method of the present invention.
Figure 26:
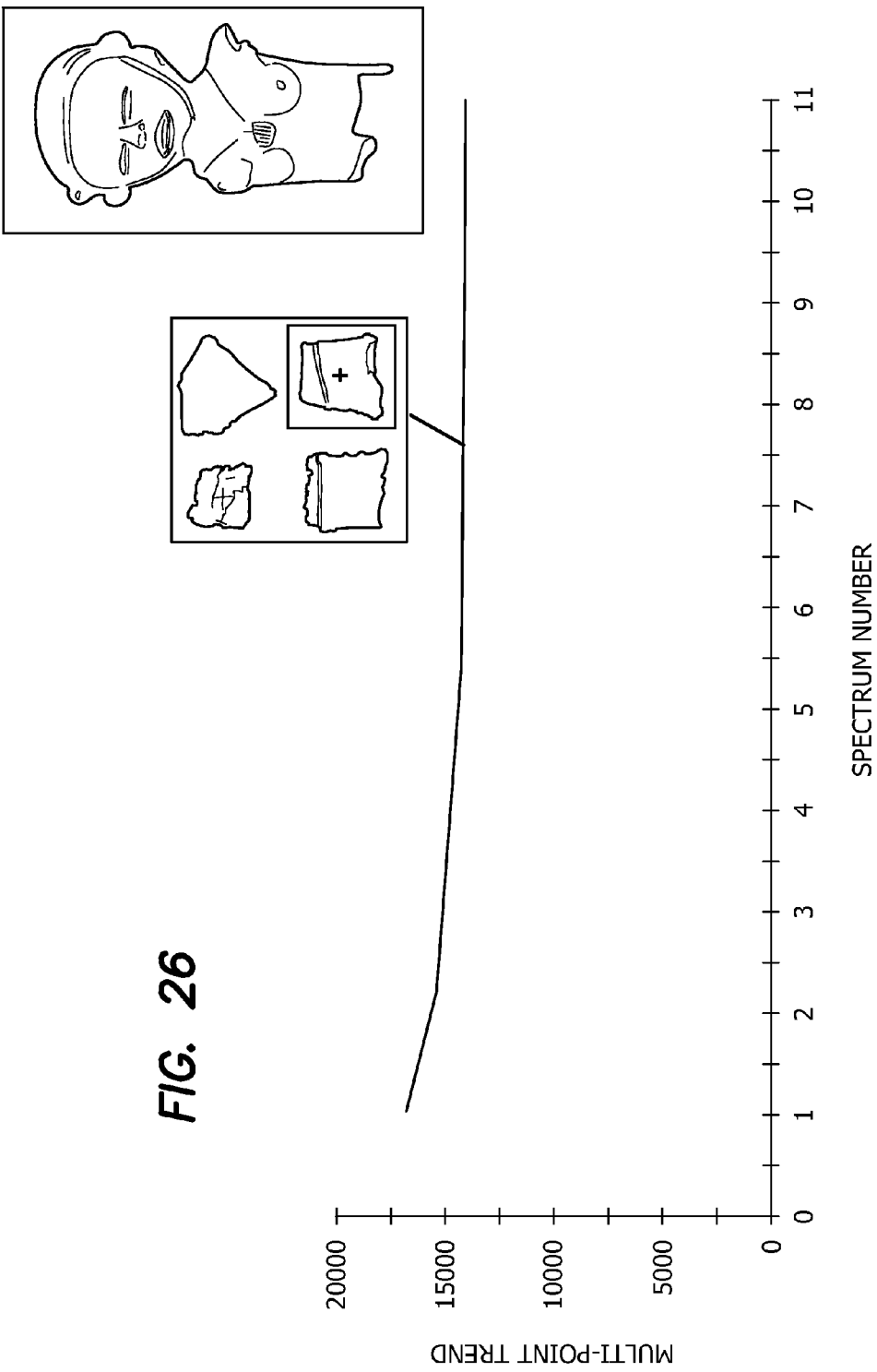
FIG. 26 is an illustration of the fluorescence measured from a heat treated pre-Columbian Vera Cruz priest fragment in accordance with the method of the present invention.

Two shards were removed from a Veracruz Priest fragment to show the pulsed Laser fluorescence data resulting from heat treatment and non-heat treatment. The method of the present invention is non-destructive to the target which will be shown in the next few examples. These tests were performed destructively to show the effect of heat treatment to quench or untrap the population of nano trapped electrons in the matrix as a result of burial and subject to background radiation damage. FIG. 26 shows the results of the heat treatment of a Veracruz priest fragment is similar and analogous to those of Experiment 14 obtained with the Mississippian pot shard. FIG. 25 shows the results of the non-heat treated shard.

Experiment 16

Figure 27:
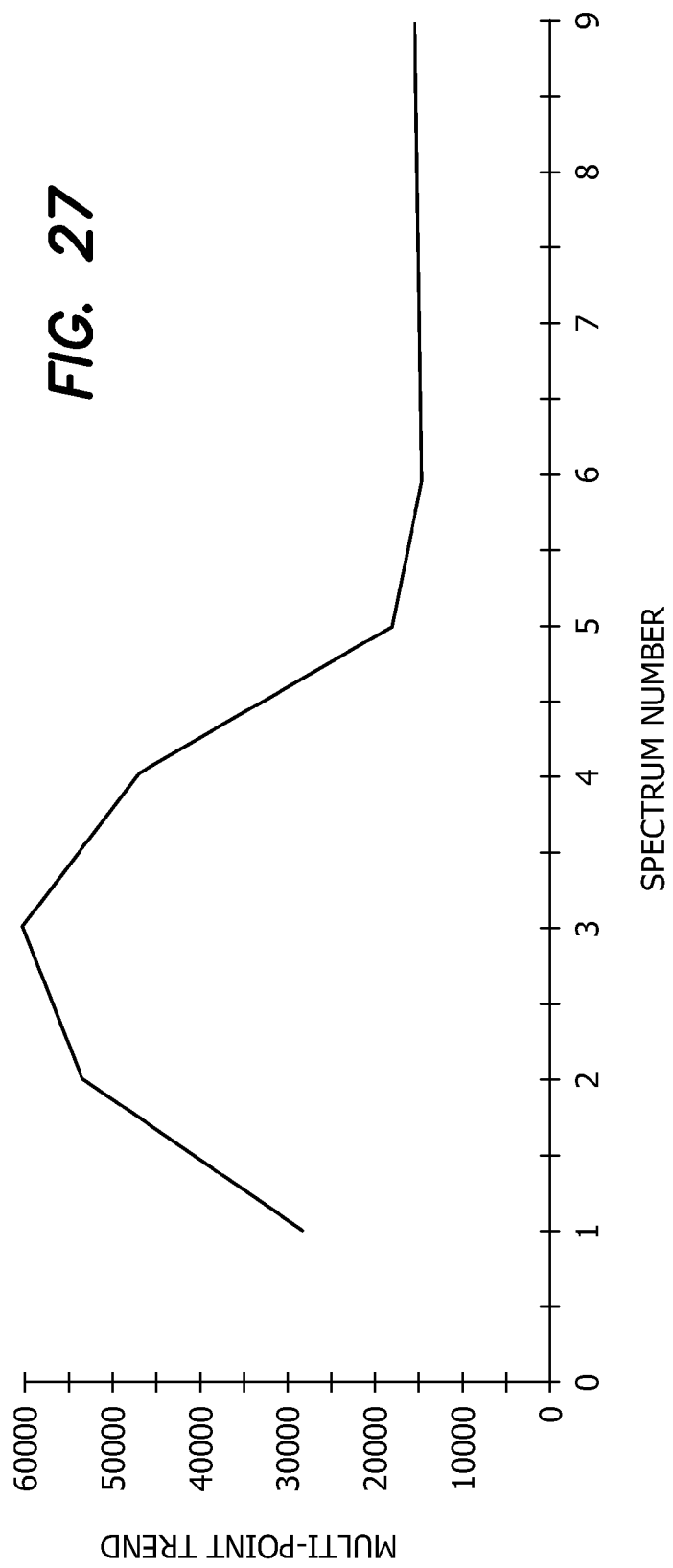
FIG. 27 is an illustration of the fluorescence measured from a Kaolin slipped Mayan poison bottle in accordance with the method of the present invention.

Non-Destructive Pulsed Laser Test of a Kaolin Slipped Mayan Poison Bottle 200Bc-100AD Referring to FIG. 27, the test comprised monitoring the approximate maximum fluorescence curve at 700 cm--1, pulse width 0.4 sec, pulse energy 0.75 maximum power. Fluorescence is observed. The area underneath the curve represents the approximate luminescent flux volume pumped out of the sample at 785 nm. The artifact is not depicted.

Experiment 17

Non-Destructive Test of a Purported Pre-Columbian Quimbaya Figure from Columbia

Figure 28:
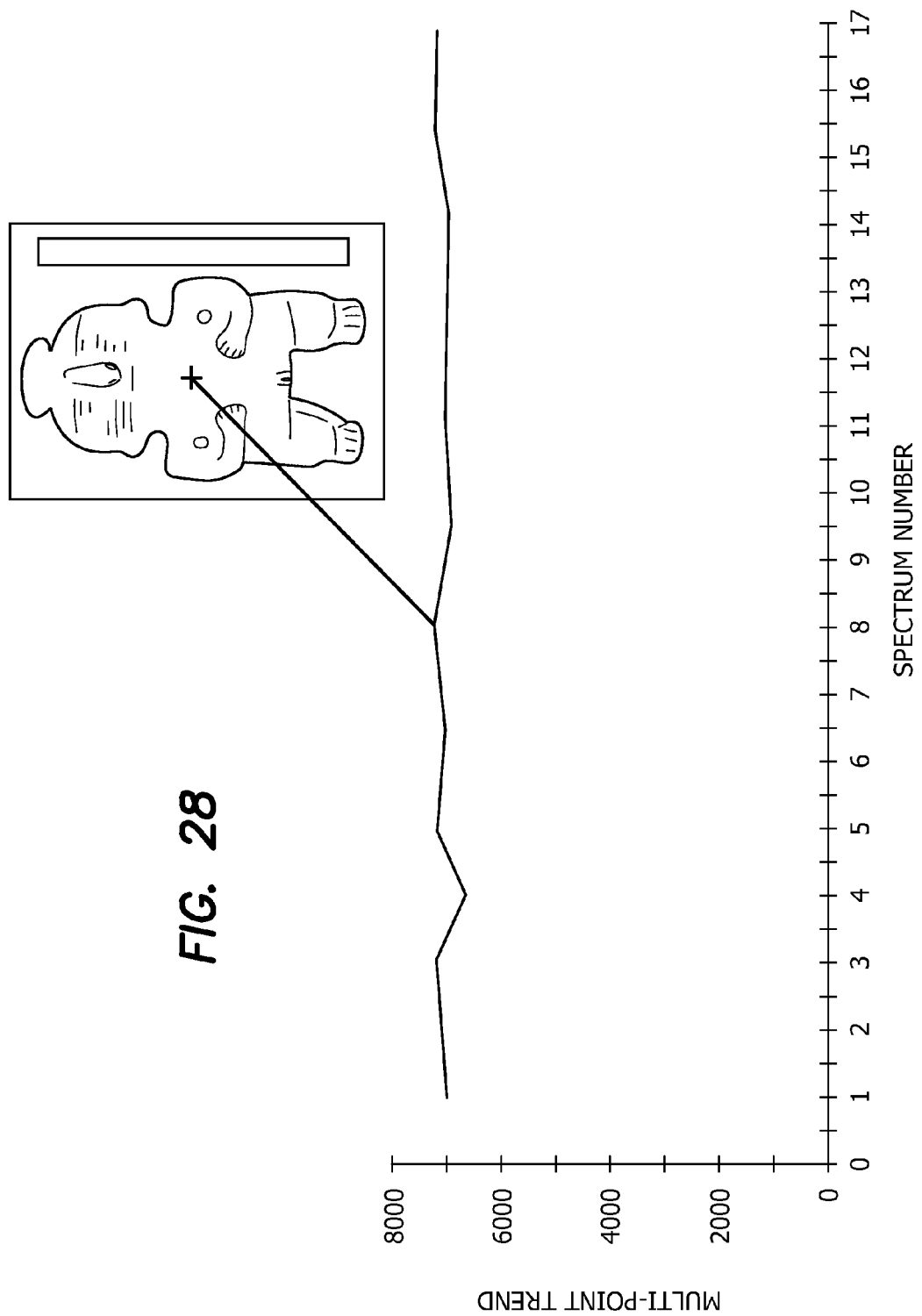
FIG. 28 is an illustration of the fluorescence measured from a fake pre-Columbian Quimbaya figure in accordance with the method of the present invention.

Referring to FIG. 28, the test used the pulsed laser technique and determined the piece to be a modern copy based on the basic flat line in the pulsed test output.

Experiment 18

Figure 29:
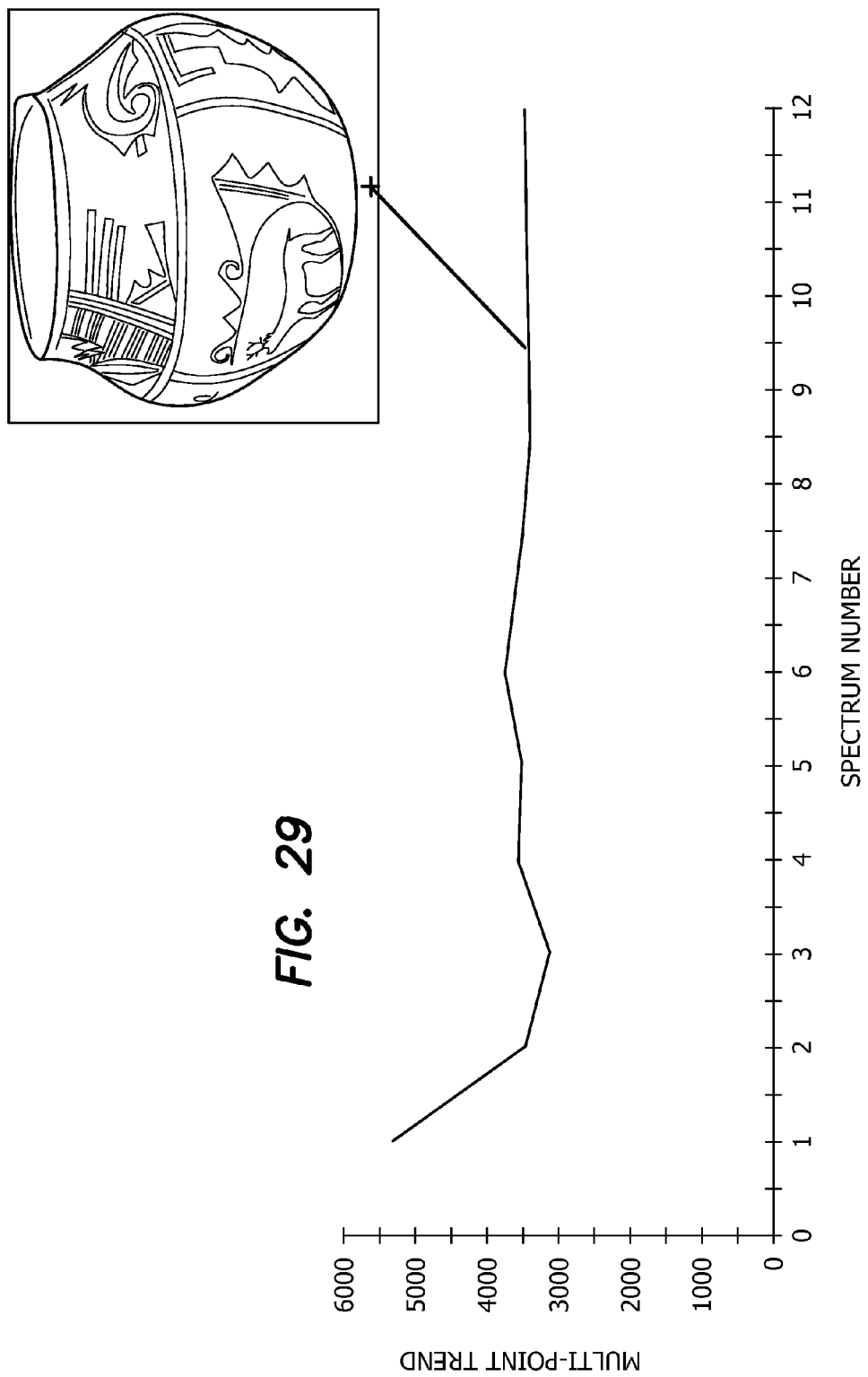
FIG. 29 is an illustration of the fluorescence measured from a Native American Zuni Olla in accordance with the method of the present invention.

Non-Destructive Pulsed Infrared Stimulated Luminescence Test (IRSL) of a Late 19th to Early 20th Century Native American Zuni Olla on a Natural Abraded Area of Base The laser energy was slightly set too high and caused the primary maxima to be formed immediately at a maximum fluorescence @5500 intensity and drops off to 3500 Fl during the second pulse, secondary maxima @ spectrum number 4 (pulse number 4) and third maxima @ spectrum number 6 @ pulse number 6. Referring to FIG. 29, the results suggest the artifact was created in the late 19th to early 20th century.

Experiment 19

Figure 30:
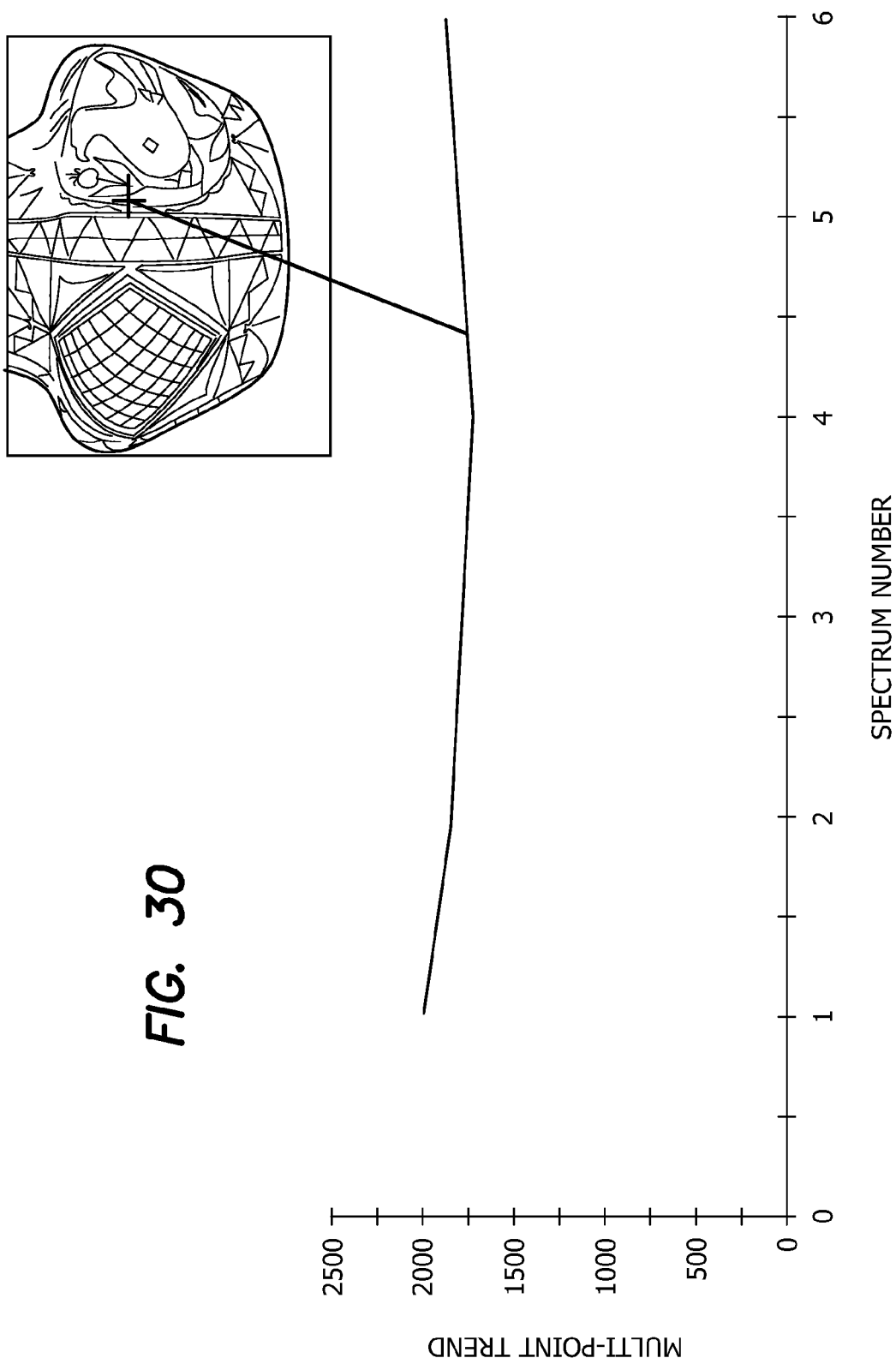
FIG. 30 is an illustration of the fluorescence measured from a fake 19th century Acoma Olla artifact in accordance with the method of the present invention.

Non-Destructive Pulsed Laser Test of a Purported Native American 19th Century Acoma Olla Referring to FIG. 30, a test was performed on a purported 19th century Acoma Olla artifact. The results yield a basic flat line in the graph which under the method of the present invention, shows the Olla to be a late 20th century copy.

Authenticity prediction using graphical integration of area under the curve of fluorescence intensity versus spectrum number or pulse number Numerical integration of the function gives a value of the total volume of nano trapped electron flux pumped out of the target. Hundreds of experiments have been performed to test the effectiveness of the technique to prove the authenticity of the terracotta or to debunk the item's authenticity. In essence, an authentic item will exhibit large gradients and some maximums throughout the test and the trend seen is the higher value of the integral, the greater the age of the object. The method of the present invention is efficient in that many places can be tested quickly in a spatially distributed surface area on the target with real time results. Accumulating data at this high rate allows one to see restored areas in the target or artifact because these areas exhibit flat line characteristics. A relative dating can result from using known archaeological specimens excavated in-situ in known sites that have been dated by the common C-14 technique. Further, If no carbon was present, then terra-cotta can be relative dated by using known TL testing of terracotta samples and comparing the pulsed laser spectrum integrals to these assigned ages. Even further, when excavated ancient terracottas are examined for mineral growths such as "Manganese blooms" (Dendritic growth of manganese oxide) or root marks and bacteriological aerobic and anaerobic decomposition of the slime left from maggot larvae trails and post eruptive mineralogical transformation like pyrite oxidation and included magnetite post eruptive oxidational observations, it can be illustrated that lack of a good IRSL integral is in tandem with lack of other mineral and bacteriological transformations aforesaid Likewise, in testing resulting with a large integral, there is a high probability of finding large amounts or even very difficult trace amounts of these transformations aforesaid. In fact in many cases, these effects are observed on places occupying 0.1-0.01% of the surface area of the item.

Experiment 20

Graphical Integration of Pulsed IRSL Data

Figure 31:
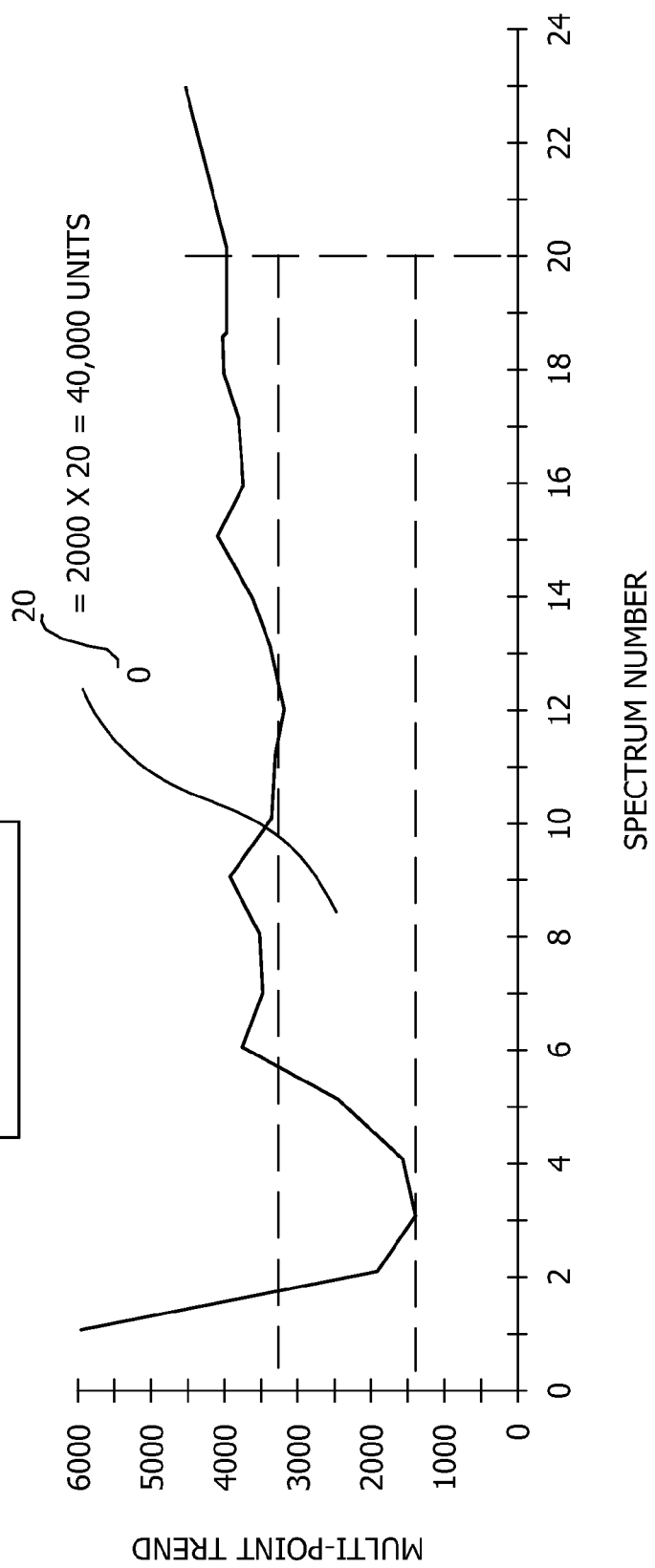
FIG. 31 is graphical integration of a pulsed IRSL test of a Honduran Plumbate pre-Columbian vessel in the age range of 850-1200AD in accordance with the method of the present invention.

FIG. 31 is an illustration of the graphical integration of a pulsed IRSL test of a Honduran Plumbate pre-Columbian vessel in the age range of 850-1200AD.

Changes may be made in the construction, operation and arrangement of the various parts, elements, steps and procedures described herein without departing from the spirit and scope of the invention as defined in the following claims.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A method for authenticating an estimated age of an archaeological artifact, comprising:
    irradiating the artifact with laser light having an energy density of between about 25 watts per square centimeter and up to 6250 watts per square centimeter;
    measuring a fluorescence spectrum emitted from the artifact; and
    determining whether the artifact's actual age is consistent with the estimated age based on the measured fluorescence.

2. The method of authentication of claim 1, further comprising irradiating an etching on the artifact with laser light.

3. The method of authentication of claim 2 wherein the first area comprises a top surface layer of the artifact.

4. The method of authentication of claim 3 wherein the second area comprises a top surface layer of the artifact having been damaged by removal of part of the surface.

5. The method of authentication of claim 4, further comprising removing a portion of the surface of the artifact.

6. The method of authentication of claim 1, further comprising:
    irradiating the artifact with laser light on a first area;
    measuring a fluorescence emitted from the first area;
    irradiating the artifact with laser light on a second area;
    measuring a fluorescence emitted from the second area; and
    comparing the fluorescence emitted from the first area with the emitted from the second area;

wherein the artifact's age is authenticated if an intensity of the fluorescence measured from the first area is greater than an intensity measured from the second area by a threshold amount.

7. The method of authentication of claim 1, further comprising:
irradiating a surface of the artifact with laser light;
measuring a fluorescence from the irradiated surface;
focusing laser light at a depth below the surface and irradiating a point in the artifact at the depth;
measuring a fluorescence from the irradiated point at depth;
comparing the measured fluorescence from the irradiated surface with the measured fluorescence from the irradiated point at depth; and
determining the authenticity of the age of artifact based on the comparison.

8. The method of authentication of claim 7, wherein determining the authenticity of the artifact based on the comparison comprises determining whether an intensity of the fluorescence measured from the irradiated surface is greater than an intensity measured from the irradiated point at depth by a threshold amount.

9. The method of authentication of claim 7, further comprising using a virtual focus head laser to irradiate the point at depth.

10. The method of authentication of claim 7, further comprising using a full contact head laser to irradiate a surface.

11. The method of claim 1, further comprising irradiating a plurality of points on the surface of the artifact and measuring the fluorescence from the plurality of points on the surface.

12. The method of claim 11, further comprising using an automated mechanical device to position a laser over the plurality of points to irradiate.

13. The method of authentication of claim 1, further comprising correlating the amount of fluorescence measured with the age of the artifact, wherein the artifact is of human origin.

14. The method of claim 13, wherein correlating the amount of fluorescence measured with the age of the artifact comprises generating a spectrum of the measured fluorescence and comparing to a library of spectra and determining the authenticity of the artifact based on the comparison.

15. A system for debunking a purported age of an artifact, comprising:
a laser configured to output light having an energy density of between about 25 watts per square centimeter and up to 6250 watts per square centimeter;
a spectrometer configured for measuring fluorescence stimulated by laser light absorption of the artifact; and
a computer configured to analyze the fluorescence measured by the spectrometer and determine whether the fluorescence measured meets a threshold amount;
wherein the computer is configured to display whether the fluorescence measured meets a threshold amount and wherein the purported age of the artifact is debunked if the measured fluorescence does not meet the threshold amount.

16. The system of claim 15, wherein the threshold amount is determined from a library of spectra from laser stimulated material of known approximate age ranges and compositions.

17. The system of claim 15, wherein the system further comprises a laser having virtual focus head and a laser having full contact head.

18. A method for debunking a purported age of an artifact, comprising:
determining the level of radiation damage in the surface of the artifact; and
comparing the level of radiation damage in the surface with the level of radiation damage in a reference material;
wherein the purported age of the artifact is debunked if the level of radiation damage in the surface of the artifact falls within a range determined by the reference material.

19. The method for debunking the age of an artifact of claim 18, wherein the reference material comprises a second object having a known age range that encompasses the purported age of the artifact, the method further comprising:
comparing the level of radiation damage in the surface of the artifact with the level of radiation damage in the surface of the second object having a known age range that encompasses the purported age of the artifact; and
wherein the purported age of the artifact is debunked if the level of radiation damage in the surface of the artifact is less than the damage in the surface of the second object having a known age range that encompasses the purported age of the artifact.

20. The method for debunking the age of an artifact of claim 18, wherein the reference material comprises the artifact itself, the method further comprising:
comparing the level of radiation damage in the surface of the artifact with the level of radiation damage in an interior point of the artifact and below the surface of the artifact; and
wherein the age of the of the artifact is debunked if the difference in radiation damage between the surface and the interior point is below a threshold amount.

* * * * *